United States Patent
Yang et al.

(10) Patent No.: US 11,473,137 B2
(45) Date of Patent: Oct. 18, 2022

(54) ALIGNMENT FREE FILTERING FOR IDENTIFYING FUSIONS

(71) Applicant: GRAIL, Inc., Menlo Park, CA (US)

(72) Inventors: Xiao Yang, San Francisco, CA (US); Hyunsung John Kim, San Francisco, CA (US); Wenying Pan, Menlo Park, CA (US); Matthew H. Larson, San Francisco, CA (US); Eric Michael Scott, Redwood City, CA (US); Pranav Parmjit Singh, Mountain View, CA (US); Mohini Jangi Desai, San Mateo, CA (US)

(73) Assignee: GRAIL, LLC, Menlo Park, CA (US)

( * ) Notice: Subject to any disclaimer, the term of this patent is extended or adjusted under 35 U.S.C. 154(b) by 858 days.

(21) Appl. No.: 16/006,704

(22) Filed: Jun. 12, 2018

(65) Prior Publication Data

US 2018/0355423 A1    Dec. 13, 2018

Related U.S. Application Data

(60) Provisional application No. 62/518,510, filed on Jun. 12, 2017.

(51) Int. Cl.

| | |
|---|---|
| G01N 33/48 | (2006.01) |
| C12Q 1/6874 | (2018.01) |
| G16H 50/20 | (2018.01) |
| G16H 50/30 | (2018.01) |
| G16B 30/00 | (2019.01) |
| G16B 5/00 | (2019.01) |
| G16B 10/00 | (2019.01) |
| G16B 20/00 | (2019.01) |
| G16B 15/00 | (2019.01) |
| G16B 25/00 | (2019.01) |
| G16B 35/00 | (2019.01) |
| G16B 40/00 | (2019.01) |
| G16B 45/00 | (2019.01) |
| G16B 50/00 | (2019.01) |
| G16B 30/20 | (2019.01) |
| G16B 30/10 | (2019.01) |
| G16B 35/10 | (2019.01) |
| G16B 35/20 | (2019.01) |

(52) U.S. Cl.
CPC .......... *C12Q 1/6874* (2013.01); *G16B 5/00* (2019.02); *G16B 10/00* (2019.02); *G16B 15/00* (2019.02); *G16B 20/00* (2019.02); *G16B 25/00* (2019.02); *G16B 30/00* (2019.02); *G16B 30/10* (2019.02); *G16B 30/20* (2019.02); *G16B 35/00* (2019.02); *G16B 35/10* (2019.02); *G16B 35/20* (2019.02); *G16B 40/00* (2019.02); *G16B 45/00* (2019.02); *G16B 50/00* (2019.02); *G16H 50/20* (2018.01); *G16H 50/30* (2018.01); *C12Q 2600/112* (2013.01); *C12Q 2600/118* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

PUBLICATIONS

Li, You. "ChimeRScope: a novel alignment-free algorithm for fusion gene prediction using paired-end short reads." Thesis (2016).*
Francis, Richard W., et al. "FusionFinder: a software tool to identify expressed gene fusion candidates from RNA-Seq data." PloS one 7.6 (2012): e39987.*
Hsieh, G. et al., "Statistical Algorithms Improve Accuracy of Gene Fusion Detection," Nucleic Acids Research, vol. 45, No. 13, May 24, 2017, 11 pages.
Newman, A. et al., "FACTERA: A Practical Method for the Discovery of Genomic Rearrangements at Breakpoint Resolution," Bioinformatics, vol. 30, No. 23, Aug. 20, 2014, pp. 3390-3393.
PCT International Search Report and Written Opinion, PCT Application No. PCT/US2018/037148, dated Sep. 18, 2018, 21 pages.
Pratas, D. et al., "An Alignment-Free Method to Find and Visualise Rearrangements Between Pairs of DNA Sequences," Scientific Reports, vol. 5, No. 1, May 18, 2015, nine pages.
Haas, B. et al., "STAR-Fusion: Fast and Accurate Fusion Transcript Detection from RNA-seq," Bioinformatics, 2017, seven pages.
Li, Y. et al., "ChineRScope: a Novel Alignment-Free Algorithm for Fusion Transcript Prediction Using Paired-Eng RNA-Seq Data," Nucleic Acids Research, vol. 45, No. 13, May 2, 2017, 18 pages.
Liu, S. et al., "Comprehensive Evaluation of Fusion Transcript Detection Algorithms and a Meta-Caller to Combine Top Performing Methods in Paired-End RNA-seq Data," Nucleic Acids Research, vol. 44, No. 5, Nov. 17, 2015, 15 pages.
Tembe, W. et al., "Open-Access Synthetic Spike-In mRNA-seq Data for Cancer Gene Fusions," BMC Genomics, 2014, 15:824, nine pages.

* cited by examiner

*Primary Examiner* — Anna Skibinsky
(74) *Attorney, Agent, or Firm* — Fenwick & West LLP

(57) ABSTRACT

Cell free nucleic acids from a test sample obtained from an individual are analyzed to identify possible fusion events. Cell free nucleic acids are sequenced and processed to generate fragments. Fragments are decomposed into kmers and the kmers are either analyzed de novo or compared to targeted nucleic acid sequences that are known to be associated with fusion gene pairs of interest. Thus, kmers that may have originated from a fusion event can be identified. These kmers are consolidated to generate gene ranges from various genes that match sequences in the fragment. A candidate fusion event can be called given the spanning of one or more gene ranges across the fragment.

27 Claims, 10 Drawing Sheets

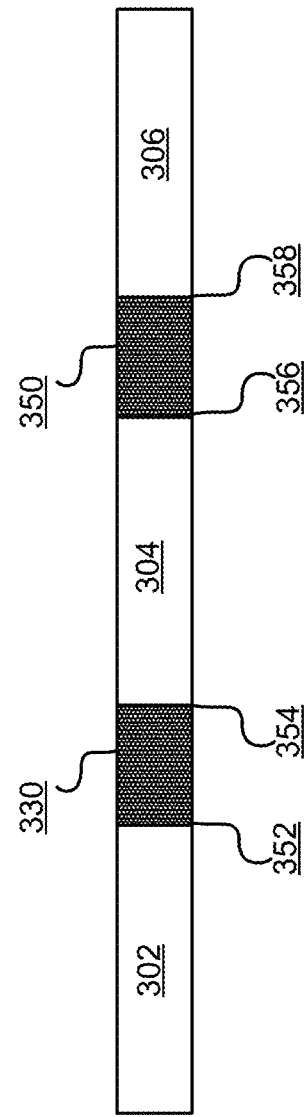
FIG. 3A
FIG. 3B

ALIGNMENT FREE FILTERING FOR IDENTIFYING FUSIONS

INTRODUCTION

A number of different methods have been developed for detecting fusion events from sequencing data, such as RNA or DNA sequencing data. Most of the existing methods have been developed for calling fusions from sequencing data obtained from a tissue sample. These methods may not be suitable for calling fusions from sequencing data obtained from a cell-free nucleic acid sample.

For non-invasive diagnostic and monitoring of cancer, cell free nucleic acid data serve as an important bio-source. However, fusion detection in such data type poses distinct challenges: the number of sequenced molecules could be at least an order of magnitude larger (~400M cell free nucleic acid molecules vs.~20M nucleic acid molecules derived from tissue), debilitating most of the existing fusion callers in compute-time and memory usage. Cancer allele fraction has been shown to be low in cell free nucleotide data compared to tissue biopsy which requires pushing the sensitivity to be significantly higher than the state-of-art methods, all of which currently have lower than a 75% true positive rate.

Generally speaking, existing fusion detection methods share common paradigms of relying on alignment of input reads against the reference genome to identify discordant alignments that may be the result of fusion events. However, when relying on alignment, once a fusion supporting read is misaligned (such as been reported as soft-clipped event), it can no longer be recovered downstream, thereby leading to reading inaccuracies. Some may further try assembling these input reads to obtain longer contigs (e.g., overlapping nucleic acid segments representing a consensus region) in hopes of more accurate alignment. The retained discordant reads are further inspected to determine the support of each fusion event. One of the important goals of these methods is to identify novel fusions that may be potentially interesting, however, this makes them very vulnerable to false positive discoveries that are of unknown clinical relevance.

SUMMARY

Disclosed herein are methods for analyzing nucleic acid sequencing data to identify and call candidate fusion events. The nucleic acid sequencing data may be generated from cell free DNA (cfDNA) or cell free RNA (cfRNA). Embodiments of the method involve processing sequencing data into fragments and further decomposing fragments into kmers. Generally, the kmers are analyzed to call a candidate fusion event. More specifically, identified kmers are consolidated to generate gene ranges from various genes that match sequences in the fragment from the sequencing data. A candidate fusion event can be called given the spanning of one or more gene ranges across the fragment.

The disclosed method enables the targeting of data (e.g., ~400M nucleic acid molecules) that is an order of magnitude larger than molecules sequenced from solid tissue biopsies. In one embodiment, fusion events are identified from fusion gene pairs that have been previously reported. This process is hereafter referred to as the targeted method. The targeted method enables the identification of fusion events that are relevant for diseases (e.g., related to cancer). The method is efficient and scalable (in terms of input number of reads) which provides for a low compute cost in terms of both computer process power and time required to run the method. In a different embodiment, fusion events are identified de novo (e.g., without guidance from previously known fusion gene pairs). This process is hereafter referred to as the de novo method. The de novo method enables the identification of new fusion events that can be indicative of disease.

Advantages of the disclosed alignment-free method of detecting fusion events include 1) improved speed (e.g., reduced runtime) in detecting fusion events and 2) reduced consumption of computer resources, such as computer memory. As an example, the method disclosed herein enables the processing of ~4000 sequence reads per thread on a computing device and consumes an estimated 15 Gigabytes/1 million read pairs. This represents an improvement in comparison to conventional alignment fusion callers, an example of which is the STAR-Fusion caller that consumes >40 Gigabytes to perform the alignment process. Further evidence of computational improvements are depicted in the Examples below.

Embodiments described herein include a computer-implemented method for identifying a candidate gene fusion from a test sample, the method comprising: receiving a data set in a computer comprising a processor and a computer-readable medium, wherein the data set comprises a plurality of sequence read pairs obtained by sequencing a test sample, and wherein the computer-readable medium comprises instructions that, when executed by the processor, cause the computer to: generate a plurality of kmers from the plurality of sequence read pairs, each kmer having a length of k nucleic acids; query each kmer within the plurality of kmers against an index structure comprising kmers decomposed from known fusion-related sequences to determine whether the kmer matches a gene segment of one or more genes; generate a plurality of gene ranges, each gene range comprising one or more kmers that map to a gene segment from a gene and map to a kmer in the index structure; determine a maximum gene span between a first gene and a second gene based on the plurality of gene ranges; and assign a candidate gene fusion event to the first gene and the second gene.

In various embodiments, the instructions to generate the plurality of kmers from the plurality of sequence read pairs further comprises instructions that, when executed by the processor, cause the computer to: process one or more of the plurality of sequence read pairs to generate a plurality of fragments; and for each fragment of the plurality of fragments, decompose the fragment into the plurality of kmers.

In various embodiments, the instructions to process one or more of the plurality of sequence read pairs to generate a plurality of fragments further comprises instructions that, when executed by the processor, cause the computer to: decompose a sequence read pair comprising a first sequence read and a second sequence read into a plurality of kmers; identify a common kmer from the plurality of kmers that occurs in the first sequence read and second sequence read; and concatenate a prefix of the first sequence read, the common kmer, and a suffix of the second sequence read. In various embodiments, the instructions to process one or more of the plurality of sequence read pairs further comprises instructions that, when executed by the processor, cause the computer to: identify an overlapping region between a first sequence read of a sequence read pair and a second sequence read of the sequence read pair; and trim an overhang of the first sequence read that is beyond the second sequence read. In various embodiments, the instructions to process one or more of the plurality of sequence read pairs further comprises instructions that, when executed by the processor, cause the computer to concatenate a first sequence read of a sequence read pair with a reverse of a second sequence read of the sequence read pair.

In some embodiments, the instructions to determine the maximum gene span further comprises instructions that, when executed by the processor, cause the computer to: for one or more pairs of gene ranges of the plurality of gene ranges, determine a score for each pair of gene ranges, wherein each of the one or more pairs of gene ranges are derived from two different genes; and determine a maximally scored pair of gene ranges, the maximally scored pair of gene ranges derived from the first gene and the second gene. In some embodiments, the instructions to determine the maximum gene span further comprises instructions that, when executed by the processor, cause the computer to order the plurality of gene ranges based on a position of each gene range.

In some embodiments, the score determined for each pair of gene ranges comprises the summation of a length of a first gene range of the pair of gene ranges, a length of a second gene range of the pair of gene ranges, and one or more lengths of gene ranges that have a lower order in comparison to the first gene range. In some embodiments, each of the first gene range and gene ranges corresponding to the one or more lengths of gene ranges are derived from a common gene. In some embodiments, the first gene range corresponds to a first gene and the second gene range is a next ordered gene range relative to the first gene range. In some embodiments, the second gene range is the next ordered gene range corresponding to the second gene.

In some embodiments, the instructions to determine the maximum gene span further comprises instructions that, when executed by the processor, cause the computer to: compare a length of the determined maximum gene span to a threshold length; and identify the first gene and the second gene as corresponding to the candidate gene fusion event based on the comparison.

In some embodiments, each kmer stored in the index structure is indexed by a fusion-related sequence. In some embodiments, each kmer stored in the index structure is indexed by a start position in the sequence that the kmer is located. In some embodiments, the plurality of kmers stored in the index structure are generated by: extracting a plurality of sequences for the previously known fusion gene pairs; and decomposing the plurality of extracted sequences into the plurality of kmers.

In various embodiments, the computer-readable medium further comprises instructions that, when executed by the processor, cause the computer to: remove one or more of the plurality of sequence read pairs that are of low complexity, wherein a low complexity sequence read pair includes one or two nucleotides that occur over a threshold percentage of all nucleotides in the sequence read pair. In some embodiments, the computer-readable medium further comprises instructions that, when executed by the processor, cause the computer to: remove one or more of the plurality of sequence read pairs that are of low complexity, wherein a low complexity sequence read pair is less than a threshold read length.

In some embodiments, the test sample comprises cell-free RNA nucleic acid fragments, and wherein the plurality of sequence read pairs comprises RNA sequencing reads. In some embodiments, the test sample comprises cell-free DNA nucleic acid fragments, and wherein the plurality of sequence read pairs comprises DNA sequencing reads. In some embodiments, the plurality of kmers stored in the index structure are generated by: generating a reference nucleic acid sequence by concatenating an exon region with an adjacent intron region; and decomposing the reference nucleic acid sequence comprising at least the concatenated exon and intron regions into kmers. In some embodiments, generating the reference nucleic acid sequence further comprises concatenating at least one exon sequence with a padding region. In some embodiments, the padding region comprises between 50-150 base pairs.

BRIEF DESCRIPTION OF THE DRAWINGS

Figure (FIG. 1 is an example flow process for processing a test sample obtained from an individual to call a fusion event, in accordance with an embodiment.

FIGS. 3A-3D each depicts an example reference nucleic acid sequence, in accordance with an embodiment.

DETAILED DESCRIPTION

Figure 1:
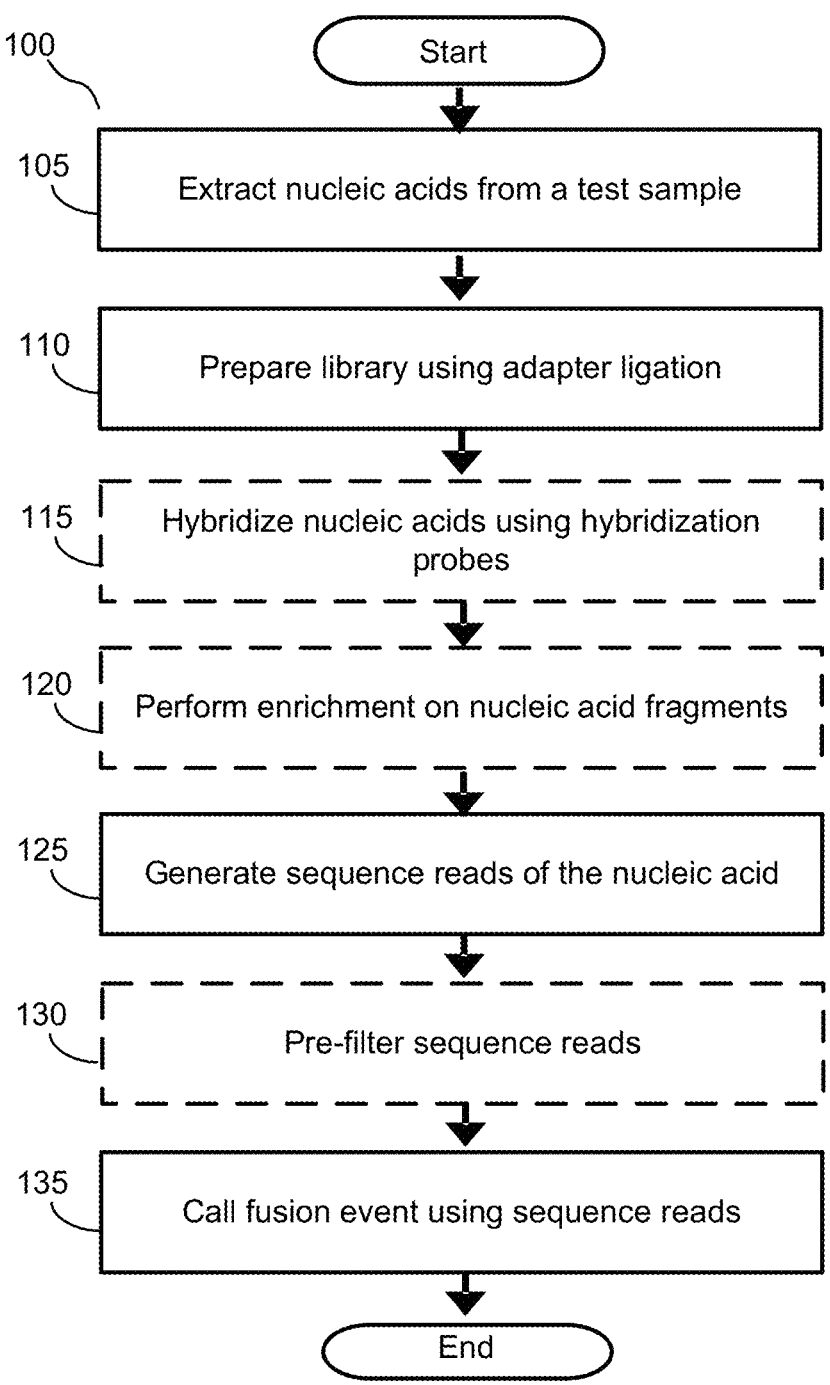

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

The term "individual" refers to a human individual. The term "healthy individual" refers to an individual presumed to not have a cancer or disease. The term "cancer subject" refers to an individual who is known to have, or potentially has, a cancer or disease.

The term "sequence reads" refers to nucleotide sequences read from a sample obtained from an individual. Sequence reads can be obtained through various methods known in the art.

The term "cell free nucleic acid," "cell free DNA," "cfDNA," "cell free RNA," or "cfRNA" refers to nucleic acid molecules that circulate in an individual's body (e.g., bloodstream) and originate from one or more healthy cells and/or from one or more cancer cells.

The term "genomic nucleic acid," "genomic DNA," or "gDNA" refers to nucleic acid including chromosomal DNA that originates from one or more healthy (e.g., non-tumor) cells. In various embodiments, gDNA can be extracted from a cell derived from a blood cell lineage, such as a white blood cell.

The term "fusion event" refers to a fusion between two separate genes at a particular location. Example causes of a fusion event include a translocation, interstitial deletion, or chromosomal inversion event.

The term "RNA fusion caller" or "RNA alignment-free filtering fusion fragment (AF4) caller" refers to the workflow process that analyzes cfRNA to identify and call candidate fusion events.

The term "DNA fusion caller" or "DNA AF4 caller" refers to the workflow process that analyzes cfDNA to identify and call candidate fusion events.

The term "targeted fusion caller," "targeted AF4 caller," or "targeted method" refers to the fusion caller, either DNA or RNA fusion caller, that identifies fusion events using previously known gene fusion events.

The term "de novo fusion caller," "de novo AF4 caller," or "de novo method" refers to the fusion caller, either DNA or RNA fusion caller, that identifies fusion events de novo, that is, without prior knowledge such as can be obtained from a database of previously known gene fusion events.

As used herein, the term "true positive" (TP) or "true positive fusion event" refers to the determination of the existence of a fusion event (e.g., an in vivo DNA breakpoint) using a fusion caller of the present disclosure in a subject whose genome includes the fusion event.

As used herein, the term "true negative" (TN) or "true negative fusion event" refers to the determination of the non-existence of fusion events using a fusion caller of the present disclosure in a subject whose genome does not include fusion events.

As used herein, the term "false positive" (FP) or "false positive fusion event" refers to the determination of the existence of a fusion event using a fusion caller of the present disclosure in a subject whose genome does not include fusion events.

As used herein, the term "sensitivity", "recall", or "true positive rate" (TPR) refers to the number of true positives divided by the sum of the number of true positives and false negatives. Sensitivity can characterize the ability of an assay or method to correctly identify a proportion of the population whose genomes include a fusion event.

As used herein, the term "specificity" or "true negative rate" (TNR) refers to the number of true negatives divided by the sum of the number of true negatives and false positives. Specificity can characterize the ability of an assay or method to correctly identify a proportion of the population whose genomes do not include a fusion event.

As used herein, the term "precision" refers to the number of true positives divided by the sum of the number of true positives and false positives.

As used herein, the term "false discovery rate" refers to the rate of type I errors in null hypothesis testing. As an example, the false discovery rate can be expressed as the number of false positives divided by the sum of the number of true positives and false positives.

As used herein, the "F1 score" refers to a measure of a test's accuracy and represents a weighted average of the precision and recall. As an example, the F1 score can be represented as 2*(precision*recall)/(precision+recall).

Methods for Generating Sequence Reads

Figure (FIG. 1 is an example flow process 100 for processing a test sample obtained from an individual to call a fusion event, in accordance with an embodiment. The method 100 includes, but is not limited to, the following steps.

At step 105, nucleic acids (DNA or RNA) are extracted from a test sample. In various embodiments, the test sample may be a sample selected from the group consisting of blood, plasma, serum, urine, fecal, and saliva samples. Alternatively, the biological sample may comprise a sample selected from the group consisting of whole blood, a blood fraction, a tissue biopsy, pleural fluid, pericardial fluid, cerebrospinal fluid, and peritoneal fluid. In one embodiment, the test sample may comprise cell-free nucleic acids, examples of which are cell-free DNA and/or cell-free RNA. For example, the test sample can be a cell-free nucleic acid sample taken from a subject's blood. In one embodiment, the cell free nucleic acid sample is extracted from a test sample obtained from a subject known to have cancer (e.g., a cancer patient), or a subject suspected of having cancer.

The following description related to fusion calling may be applicable to both DNA and RNA types of nucleic acid sequences. In various embodiments, nucleic acids are extracted from the test sample through a purification process. In general, any known method in the art can be used for purifying nucleic acids. For example, nucleic acids can be isolated by pelleting and/or precipitating the nucleic acids in a tube. In some embodiments, nucleic acids can be further processed. For example, the cell free nucleic acid extracted from the test sample can be RNA that is then converted to DNA using reverse transcriptase.

At step 110, a sequencing library is prepared. During library preparation, adapters, for example, include one or more sequencing oligonucleotides for use in subsequent cluster generation and/or sequencing (e.g., known P5 and P7 sequences for used in sequencing by synthesis (SBS) (Illumina, San Diego, Calif.)) are ligated to the ends of the nucleic acid molecules through adapter ligation. In one embodiment, unique molecular identifiers (UMI) are added to the extracted nucleic acids during adapter ligation. The UMIs are short nucleic acid sequences (e.g., 4-10 base pairs) that are added to ends of nucleic acids during adapter ligation. In some embodiments, UMIs are degenerate base pairs that serve as a unique tag that can be used to identify sequence reads obtained from nucleic acids. As described later, the UMIs can be further replicated along with the attached nucleic acids during amplification, which provides a way to identify sequence reads that originate from the same original nucleic acid segment in downstream analysis.

Steps 115 and 120 may be optionally performed. As one example, steps 115 and 120 are performed when generating sequence reads through a targeted gene panel. As another example, steps 115 and 120 are performed when generating sequence reads through whole exome sequencing. Conversely, steps 115 and 120 are not performed when generating sequence reads through whole genome sequencing.

Specifically, at step 115, hybridization probes are used to enrich a sequencing library for a selected set of nucleic acids. Hybridization probes can be designed to target and hybridize with targeted nucleic acid sequences to pull down and enrich targeted nucleic acid molecules that may be informative for the presence or absence of cancer (or disease), cancer status, or a cancer classification (e.g., cancer type or tissue of origin). In accordance with this step, a plurality of hybridization pull down probes can be used for a given target sequence or gene. The probes can range in length from about 40 to about 160 base pairs (bp), from about 60 to about 120 bp, or from about 70 bp to about 100 bp. In one embodiment, the probes cover overlapping portions of the target region or gene. For targeted gene panel sequencing, the hybridization probes are designed to target and pull down nucleic acid molecules that derive from specific gene sequences that are included in the targeted gene panel. For whole exome sequencing, the hybridization probes are designed to target and pull down nucleic acid molecules that derive from exon sequences in a reference genome.

After a hybridization step 115, the hybridized nucleic acid molecules are enriched 120. For example, the hybridized nucleic acid molecules can be captured and amplified using PCR. The target sequences can be enriched to obtain enriched sequences that can be subsequently sequenced. For example, as is well known in the art, a biotin moiety can be added to the 5'-end of the probes (i.e., biotinylated) to facilitate pulling down of target probe-nucleic acids complexes using a streptavidin-coated surface (e.g., streptavidin-coated beads). This improves the sequencing depth of sequence reads.

In step 125, the nucleic acids are sequenced to generate sequence reads. Sequence reads may be acquired by known means in the art. For example, a number of techniques and platforms obtain sequence reads directly from millions of individual nucleic acid (e.g., DNA such as cfDNA or gDNA or RNA such as cfRNA) molecules in parallel. Such techniques can be suitable for performing any of targeted gene panel sequencing, whole exome sequencing, whole genome sequencing, targeted gene panel bisulfite sequencing, and whole genome bisulfite sequencing.

As a first example, sequencing-by-synthesis technologies rely on the detection of fluorescent nucleotides as they are incorporated into a nascent strand of DNA that is complementary to the template being sequenced. In one method, oligonucleotides 30-50 bases in length are covalently anchored at the 5' end to glass cover slips. These anchored strands perform two functions. First, they act as capture sites for the target template strands if the templates are configured with capture tails complementary to the surface-bound oligonucleotides. They also act as primers for the template directed primer extension that forms the basis of the sequence reading. The capture primers function as a fixed position site for sequence determination using multiple cycles of synthesis, detection, and chemical cleavage of the dye-linker to remove the dye. Each cycle consists of adding the polymerase/labeled nucleotide mixture, rinsing, imaging and cleavage of dye.

In an alternative method, polymerase is modified with a fluorescent donor molecule and immobilized on a glass slide, while each nucleotide is color-coded with an acceptor fluorescent moiety attached to a gamma-phosphate. The system detects the interaction between a fluorescently-tagged polymerase and a fluorescently modified nucleotide as the nucleotide becomes incorporated into the de novo chain.

Any suitable sequencing-by-synthesis platform can be used to identify mutations. Sequencing-by-synthesis platforms include the Genome Sequencers from Roche/454 Life Sciences, the GENOME ANALYZER from Illumina/SOLEXA, the SOLID system from Applied BioSystems, and the HELISCOPE system from Helicos Biosciences. Sequencing-by-synthesis platforms have also been described by VisiGen Biotechnologies. In some embodiments, a plurality of nucleic acid molecules being sequenced is bound to a support (e.g., solid support). To immobilize the nucleic acid on a support, a capture sequence/universal priming site can be added at the 3' and/or 5' end of the template. The nucleic acids can be bound to the support by hybridizing the capture sequence to a complementary sequence covalently attached to the support. The capture sequence (also referred to as a universal capture sequence) is a nucleic acid sequence complementary to a sequence attached to a support that may dually serve as a universal primer.

As an alternative to a capture sequence, a member of a coupling pair (such as, e.g., antibody/antigen, receptor/ligand, or the avidin-biotin pair) can be linked to each molecule to be captured on a surface coated with a respective second member of that coupling pair. Subsequent to the capture, the sequence can be analyzed, for example, by single molecule detection/sequencing, including template-dependent sequencing-by-synthesis. In sequencing-by-synthesis, the surface-bound molecule is exposed to a plurality of labeled nucleotide triphosphates in the presence of polymerase. The sequence of the template is determined by the order of labeled nucleotides incorporated into the 3' end of the growing chain. This can be done in real time or can be done in a step-and-repeat mode. For real-time analysis, different optical labels to each nucleotide can be incorporated and multiple lasers can be utilized for stimulation of incorporated nucleotides.

Massively parallel sequencing or next generation sequencing (NGS) techniques include synthesis technology, pyrosequencing, ion semiconductor technology, single-molecule real-time sequencing, sequencing by ligation, or paired-end sequencing. Examples of massively parallel sequencing platforms are the Illumina HISEQ or MISEQ, ION PERSONAL GENOME MACHINE, the PACBIO RSII sequencer or SEQUEL System, Qiagen's GENEREADER, and the Oxford MINION. Additional similar current massively parallel sequencing technologies can be used, as well as future generations of these technologies.

In various embodiments, a sequence read is comprised of a read pair denoted as $R_1$ and $R_2$. For example, the first read $R_1$ may be sequenced from a first end of a nucleic acid molecule whereas the second read $R_2$ may be sequenced from the second end of the nucleic acid molecule.

Optionally, at step 130, the sequence reads generated at step 125 undergo a pre-filtering step to remove sequence reads. Generally, step 130 is performed depending on whether DNA or RNA is extracted from the test sample at step 105. For example, if the flow process 100 is a DNA fusion caller, then step 130 is performed to pre-filter sequence reads that are generated from DNA extracted from the test sample. Alternatively, if the flow process 100 is a RNA fusion caller, then step 130 is not performed. The pre-filtering process is described in further detail below in relation to FIG. 7.

Following step 130, sequence reads are processed using a computational analysis to call a fusion event. Such a computational analysis is now described in relation to FIG. 2, which depicts an overall workflow of identifying fusion pair events, in accordance with an embodiment. Generally, the computational analysis is an alignment-free filtering fusion fragment (AF4) caller where the sequence reads generated at step 125 need not be aligned to a reference genome. In one embodiment, the computational analysis is an AF4 caller that uses the targeted method (e.g., targeted AF4 caller) to predict the presence of gene fusion event(s) in the individual by utilizing previously known gene fusion events. Thus, the targeted AF4 caller need not analyze the entire genome to identify fusion events. In another embodiment, the computational analysis is an AF4 caller that uses the de novo method (e.g., de novo AF4 caller) to predict the presence of gene fusion event(s) in the individual without prior knowledge. Here, the de novo AF4 caller can potentially identify fusion events at different locations in the genome that the targeted AF4 caller may miss. Particular differences between the targeted AF4 caller and the de novo AF4 caller are described in further detail below in relation to steps 215 and 220.

At step 205, sequence reads are obtained (e.g., from step 125). At step 210, given sequencing data, the sequencing data are streamed in batches such that a limited number of records of the sequencing data are loaded in the memory that can be processed in parallel. Records may include a sequence read, an example of which is a pair of sequence reads, hereafter referred to as read pair (e.g., $r_1$ and $r_2$).

Steps 215 and 220 are optionally performed and utilize information previously known to be associated with fusion events. Namely, steps 215 and 220 are performed for the targeted AF4 caller whereas steps 215 and 220 are not performed for the de novo AF4 caller. Specifically, at step 215, known cancer-related fusion events can be obtained. For example, a target list of known gene fusions (herein referred to as "fusion-related genes") can be obtained from one or more publicly available databases and the gene pairs associated with each fusion event identified (e.g., identified by their gene symbols). In one example, the targeted fusions are cancer-related fusion events and the list of fusion-related genes and associated fusion-related gene pairs are obtained from the Catalog of Somatic Mutations in Cancer (COSMIC) database.

At step 220, the cancer-related fusion events are analyzed to obtain fusion genes and gene pairs. Fusion genes refer to hybrid genes that are formed from two previously separate genes. A gene pair refers to the two previously separate genes that lead to a fusion gene. Here, the fusion genes and the gene pairs correspond to cancer-related fusion events and as such, can be informative for predicting cancer-related activity in an individual. The fusion gene and gene pair can be subsequently used (e.g., at step 230) to guide the generation of an indexing structure.

Steps 225 and 230 generally establish the search space for subsequent identification of fusion events in newly acquired RNA or DNA sequencing data from a test sample of interest. For example, for a targeted AF4 caller, steps 225 and 230 use the obtained fusion gene and gene pairs corresponding to the known cancer-related fusion events determined at step 220 to establish a reduced search space. Therefore, candidate fusion events identified using the targeted AF4 caller correspond to known cancer-related fusion events. On the contrary, for a de novo AF4 caller, steps 225 and 230 establish a search space that can include the entirety of the genome. Therefore, candidate fusion events identified using the de novo AF4 caller can be fusion events across the entirety of the genome.

At step 225, reference nucleic acid sequences are generated. A reference nucleic acid sequence can include one of RNA sequences or DNA sequences depending on whether the AF4 caller is a RNA fusion caller or a DNA fusion caller. Generally, the totality of reference nucleic acid sequences represent an initial search space that possible fusion events are subsequently searched against. In particular embodiments, if the AF4 caller is a RNA fusion caller, a reference nucleic acid sequence includes messenger RNA sequences of a transcriptome. Therefore, the reference nucleic acid sequence includes sequences that encode for proteins, which enables subsequent identification of candidate fusion events that affect encoded proteins. In some embodiments, if the AF4 caller is a DNA fusion caller, a reference nucleic acid sequence includes DNA sequences across a region of the genome, such as a chromosome. The reference nucleic acid sequence including DNA sequences across the region of the genome can be used to identify candidate fusion events that affect that particular region of the genome.

For a DNA AF4 caller, in some embodiments, a reference nucleic acid sequence can include exonic DNA sequences. Thus, this reference nucleic acid sequence can be used to identify candidate fusion events that affect exonic DNA sequences. Such an embodiment is described below in relation to FIG. 3A. In some embodiments, the reference nucleic acid sequence includes, in addition to exonic DNA sequences, intronic DNA sequences. Thus, this reference nucleic acid sequence can be used to identify candidate fusion events that affect both exonic and intronic DNA sequences. Such an embodiment is described below in relation to FIG. 3B. In some embodiments, the reference nucleic acid sequence includes a combination of exonic DNA sequences, intronic DNA sequences, and additional nucleotide bases within padding regions. Padding regions can be nucleic acid sequences that are known to be unlikely associated with gene fusion events such as repeating nucleic acid sequences or other intronic regions. Thus, this reference nucleic acid sequence can be used to identify candidate fusion events that affect exonic DNA sequences, intronic DNA sequences, as well as junctions between exonic/intronic DNA sequences. Such embodiments are described below in relation to FIGS. 3C and 3D.

Reference is first made to FIG. 3A, which depicts an example reference nucleic acid sequence 310A, in accordance with a first embodiment. Here, the example reference nucleic acid sequence 310A includes exonic DNA sequences. Specifically, FIG. 3A depicts a reference DNA sequence 310A where each of region 302, 304, and 306 refers to an exonic region. Therefore, the reference nucleic acid sequence shown in FIG. 3A can be generated by concatenating nucleic acid sequences of exonic region 302 with nucleic acid sequences of exonic region 304 and nucleic acid sequences of exonic region 306.

FIG. 3B depicts an example reference nucleic acid sequence 310B, in accordance with a second embodiment. Here, the example reference nucleic acid sequence 310B includes both exonic DNA sequences and intronic DNA sequences. FIG. 3B depicts exonic regions 302, 304, and 306 as well as intronic regions 330 and 350. In particular, intronic region 330 is concatenated with exonic regions 302 and 304, whereas intronic region 350 is concatenated with exonic regions 304 and 306. In various embodiments, the intronic regions 330 and 350 can be of various sizes (e.g., larger than exonic regions 302, 304, and/or 306). FIG. 3B further depicts concatenation points, hereafter referred to as junctions, between an exonic region and an intronic region. Specifically, a splicing junction refers to a concatenation point between an exonic region and an intronic region. As shown in FIG. 3B, splicing junctions 352 and 354 refer to points between intronic region 330 and exonic regions 302 and 304, respectively. Splicing junctions 356 and 358 refer to points between intronic region 350 and exonic regions 304 and 306, respectively.

Figure 3C:
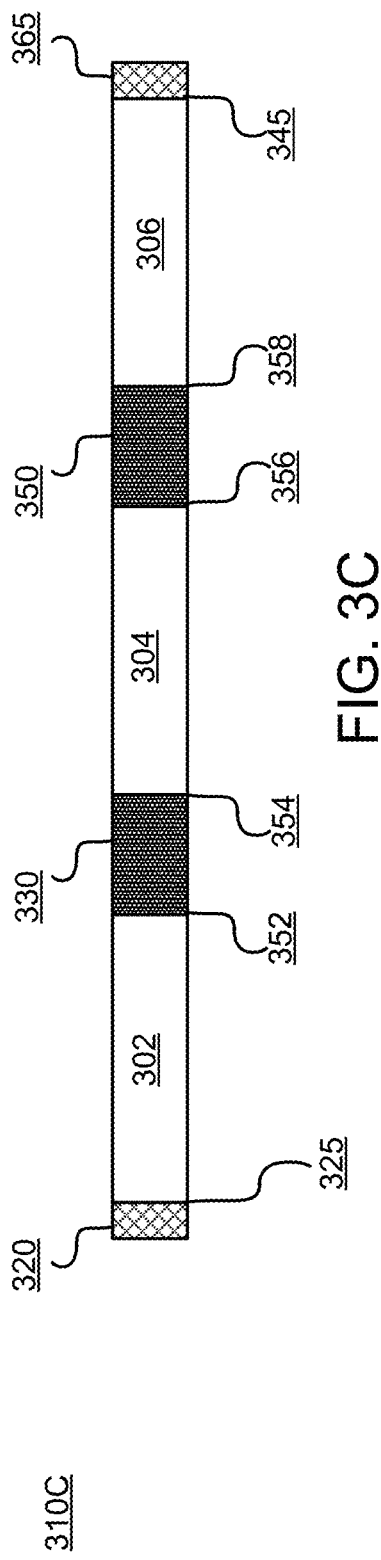

FIG. 3C depicts an example reference nucleic acid sequence 310C, in accordance with a third embodiment. Here, the example reference nucleic acid sequence 310C includes exonic DNA sequences, intronic DNA sequences, and further includes padding regions. In various embodiments, padding regions can include 10, 20, 25, 30, 35, 40, 45, 50, 55, 60, 65, 70, 75, 80, 85, 90, 95, or 100 nucleotide base pairs. The inclusion of intronic regions and padding regions improves sensitivity of the fusion caller as fusion events that occur within or at the boundary of intronic regions can be additionally detected. FIG. 3C depicts exonic regions 302, 304, and 306, intronic regions 330 and 350, as well as padding regions 320 and 365. In particular, intronic region 330 is concatenated with exonic regions 302 and 304, whereas intronic region 350 is concatenated with exonic regions 304 and 306. Padding region 320 is concatenated with exonic region 302 and padding region 365 is concatenated with exonic region 306. Although padding regions 320 and 365 are depicted at the ends of the reference nucleic acid 310C shown in FIG. 3C, in other embodiments, the padding regions can be located elsewhere. Additionally, in various embodiments, the intronic regions 330 and 350 can be of various sizes (e.g., larger than exonic regions 302, 304, and/or 306). FIG. 3C further depicts padding junctions, which each refer to a concatenation point between a padding region and an exonic region. As shown in FIG. 3C, padding junction 325 refers to the point between padding region 320 and exonic region 302 and padding junction 345 refers to the point between exonic region 306 and padding region 365.

In particular embodiments, a reference nucleic acid sequence includes a combination of exonic DNA sequences and portions of adjacent exonic, intronic, and padding nucleic acid sequences. More specifically, each portion of an adjacent exonic nucleic acid sequence, intronic nucleic acid sequence, or padding nucleic acid sequence can include 10, 20, 25, 30, 35, 40, 45, 50, 55, 60, 65, 70, 75, 80, 85, 90, 95, or 100 nucleotide base pairs. Each pair of adjacent nucleic acid sequences includes a junction (e.g., a splicing junction or a padding junction). By including padding junctions and splicing junctions within a reference nucleic acid sequence, this enables detection of false positive candidate fusion events that are often falsely detected at junctions.

Figure 3D:
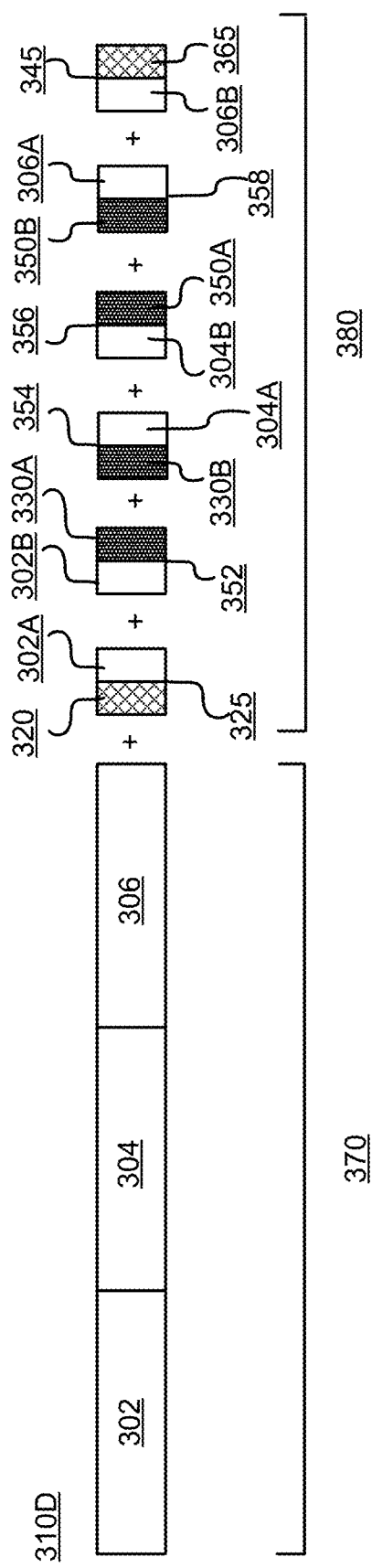

FIG. 3D depicts an example reference nucleic acid sequence 310D, in accordance with a third embodiment. FIG. 3D depicts a reference nucleic acid sequence 310D that includes a combination of exonic regions, portions of adjacent exonic and intronic regions, and padding regions. More specifically, a first section 370 of the reference nucleic acid sequence 310D includes concatenated exonic regions 302, 304 and 306. Here, the first section 370 of the reference nucleic acid sequence 310C represents reference nucleic acid sequence 310A shown in FIG. 3A. Additionally, a second section 380 of the reference nucleic acid sequence 310D shown in FIG. 3D includes portions of nucleic acid sequences on either side of different junctions, such as the padding junctions and/or splicing junctions shown in FIG. 3C.

In particular, the second section 380 of the reference nucleic acid sequence 310D includes the padding junction 325 with flanking nucleic acid sequences that include the padding region 320 and a first portion of the exonic region 302 (e.g., portion 302A). Additionally, the second section 380 includes splicing junction 352 with flanking nucleic acid sequences that include a second portion of the exonic region 302 (e.g., portion 302B) and a first portion of the intronic region 330 (e.g., portion 330A), splicing junction 354 with flanking nucleic acid sequences that include a second portion of the intronic region 330 (e.g., portion 330B) and a first portion of the exonic region 304 (e.g., portion 304A), splicing junction 356 with flanking nucleic acid sequences that include a second portion of the exonic region 304 (e.g., portion 304B) and a first portion of the intronic region 350 (e.g., portion 350A), splicing junction 358 with flanking nucleic acid sequences that include a second portion of the intronic region 350 (e.g., portion 350B) and a first portion of the exonic region 306 (e.g., portion 306A), and padding junction 345 with flanking nucleic acid sequences that include a second portion of the exonic region 306 (e.g., portion 306B) and padding region 365.

Altogether, the example embodiments shown in FIGS. 3A-3D each depicts one example of a reference nucleic acid sequence. More generally, a reference nucleic acid sequence can include one or more of exonic regions, intronic regions, and padding regions. Additionally, although the example embodiments in FIGS. 3A-3D depict particular concatenations between exonic regions, intronic regions, and/or padding regions, the regions can be differently organized and concatenated than as depicted.

Returning to FIG. 2, at step 230, reference nucleic acid sequences are analyzed to generate fusion-related sequences that establishes the final search space upon which candidate fusion events are subsequently identified from.

In one embodiment, where the fusion caller is a targeted fusion caller, the reference nucleic acid sequences are compared to the fusion-related gene pairs that were identified at step 220. Reference nucleic acid sequences that correspond to fusion-related gene pairs are maintained whereas reference nucleic acid sequences that do not correspond to fusion-related gene pairs are removed. Here, the reference nucleic acid sequences that remain, which represent the generated fusion-related sequences, establishes a final search space that includes sequences corresponding to known fusion-related genes. In other words, the targeted fusion caller uses previously known fusion-related gene information to reduce the search space to the fusion-related sequences such that the fusion caller can identify candidate fusion events in this reduced search space.

In another embodiment, where the fusion caller is a de novo fusion caller, the reference nucleic acid sequences generated at step 225 serve as the fusion-related sequences that establishes the search space. In other words, the de novo fusion caller does not use previously known fusion-related gene information and instead, the established search space at step 230 is the full initial search space represented by the totality of reference nucleic acid sequences generated at step 225. Therefore, the de novo fusion callers can potentially identify addition fusion events that are not previously known.

Further, at step 230, an indexing structure is built in working or persistent memory of a computer. In one embodiment, the indexing structure is a hash table, however other techniques for building the indexing structure are known to those of skill in the art. As a specific example, the indexing structure can be built using a hashing strategy where fusion-related sequences that establish the search space are each decomposed to overlapping substrings with length k (i.e., kmers) and each kmer is indexed by a sequence (e.g., geneID) and location (e.g., corresponding start position in the sequence). Each kmer can then be used as a key to look up in the indexing structure a possible geneID (e.g., g') and position (e.g., p'). The kmer length (k) is selected such that a kmer does not randomly occur in sequences corresponding to the targeted fusions and meanwhile, it is trusted to be the minimum length evidence of a fusion event. In one example, a kmer length range is from about 5 bases to about 20 bases, from about 7 bases to about 18 bases, or from about 10 bases to about 17 bases. In some embodiments, a kmer size range from about 12 bases to about 15 bases is sufficient to cover one side of a junction in a fusion sequence. Other kmer lengths may also be used.

Analyzing Sequence Reads to Identify Fusion Events

In process 235, the sequence reads from step 205 are evaluated as to whether the sequence reads support one or more fusion events. The process 235 is hereafter referred to as the Alignment Free Filtering Fusion Fragment (AF4) Caller and can be implemented for calling fusion events from either cfDNA or from cfRNA. In various embodiments, the sequencing data includes a single read or a read pair ($r_1$, $r_2$). When a read pair supports a fusion event, one of the following items (1)-(3) holds: (1) $r_1$ and $r_2$ belong to different genes that form the fusion pair and, in this case/item, neither $r_1$ nor $r_2$ span the breakpoint, (2) either $r_1$ or $r_2$ spans the fusion junction whereas the other belongs solely one of the genes involved in the fusion event, (3) in cases when the fragment is nucleic acid molecule is small such that $r_1$ and $r_2$ overlap, both of them span the fusion junction and derive from both genes.

In one specific embodiment, the above general criteria are translated into the following two specific spanning criteria for ($r_1$, $r_2$) to support a known fusion event: (1) a large portion $P_s$ (e.g. 50%, where subscript s stands for single) of either $r_1$ or $r_2$ should belong to one of a fusion genes involved in the fusion event, and (2) the entire $P_d$ (e.g. 100%, where subscript d stands for dual) portion of $r_1$ and $r_2$ should belong to both genes involved in the fusion event. The exact values of $P_s$ and $P_d$ may be reduced to account for sequence errors, or otherwise vary by implementation. In addition, as it is hard to confirm the validity of a breakpoint spanning read if the prefix or suffix of the read on either side of the junction is too small, an additional criterion can be imposed that (3) a fusion gene should be supported by a minimum length by either $r_1$ or $r_2$.

The aforementioned general criteria (and specific example presented thereafter) are necessary conditions for ($r_1$, $r_2$) to be a support of a fusion event but they are not sufficient criteria. In other words, the aforementioned criteria do not expect to rule out false positives but expect to increase specificity when imposed together.

At step 250, low complexity paired-end reads are ignored. Low complexity paired-end reads can be identified based on one or more criteria. An example of a criterion includes when any single, double, or triple nucleotides occur over a certain percentage (e.g., over 90%) in both paired end reads.

Generating a Fragment from Sequence Reads

Figure 4A:
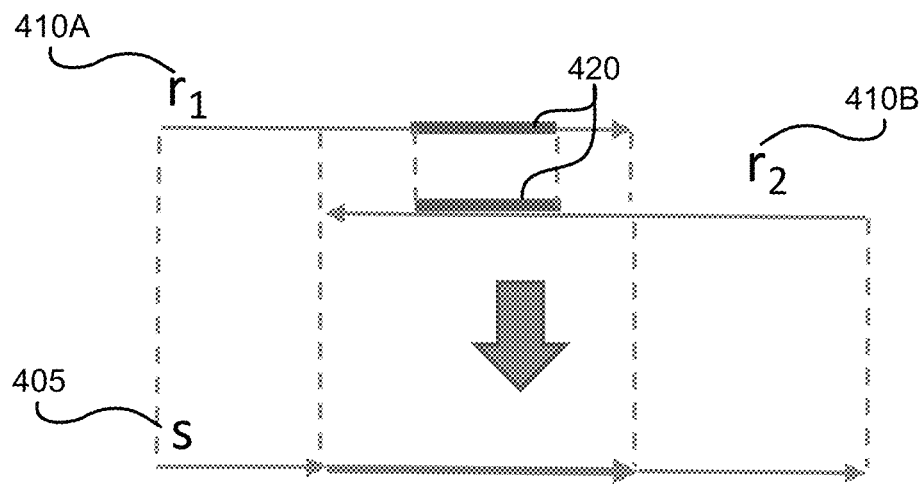
FIG. 4A-4C depict example stitching and trimming processes for generating a read fragment s from a read pair $r_1$ and $r_2$, in accordance with an embodiment.
Figure 4B:
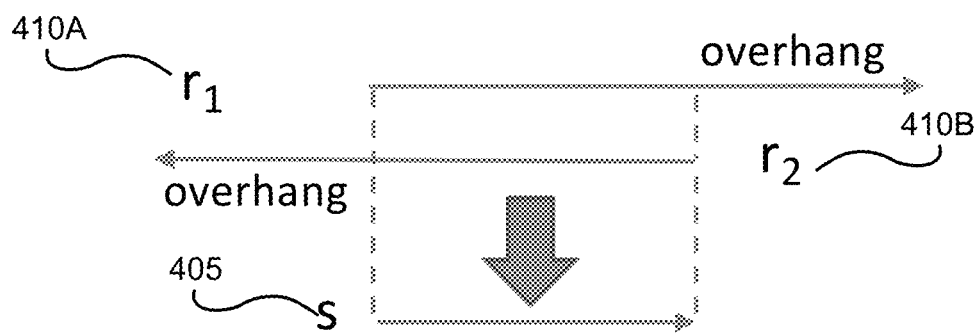
Figure 4C:
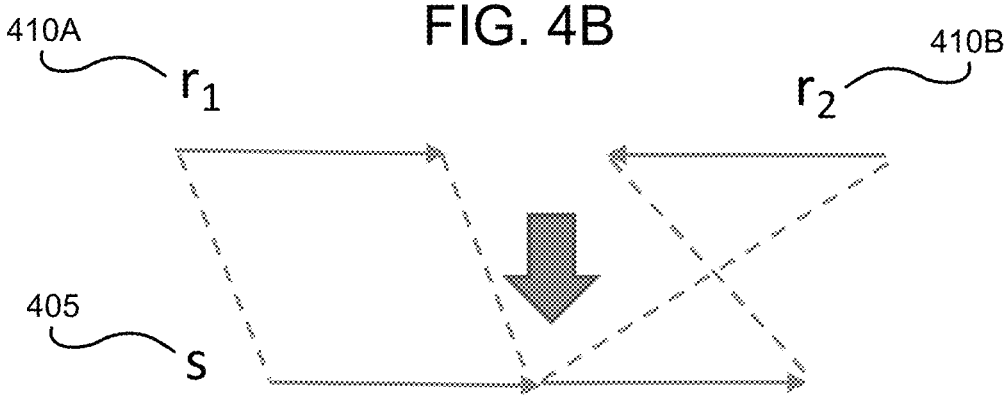

Read pairs that remain after removal of low complexity sequence reads undergo further processing in step 255. For example, this may entail stitching or overhang trimming of the read pair ($r_1$, $r_2$). FIG. 4A-4C depict example stitching and trimming processes for generating a fragment s 405 from a read pair $r_1$ 410A and $r_2$ 410B, in accordance with an embodiment.

As shown in FIGS. 4A-4C, $r_1$ 410A and $r_2$ 410B are represented as arrows facing each other denoting the forward and reverse complement strands. The read pair ($r_1$, $r_2$) are evaluated to determine whether they should be stitched into the same fragment s 405: $r_1$ and $r_2$ are decomposed to kmers, and each common kmer anchors the suffix—prefix alignment of $r_1$ 410A and $r_2$ 410B (FIG. 4A). If the similarity of the alignment passes a certain threshold, stitching is applied. As shown in FIG. 4A, the overlapping regions 420 between the read pair denotes one of the shared kmers (e.g., overlap) between them, which is an anchor for suffix-prefix alignment. Therefore, the stitched fragment s 405 is a concatenation of a prefix of $r_1$ 410A, overlap, and a suffix of $r_2$ 410B.

In another scenario, if the 3' end of $r_1$/$r_2$ extends beyond the 5' of $r_2$/$r_1$ (overhang), fragment s 405 becomes the overlapping region. This is the scenario shown in FIG. 4B where $r_1$ 410A and/or $r_2$ 410B extends beyond the 5' region of the other read. The overhang is trimmed, and fragment s 405 is the overlap.

In another scenario, if $r_1$ 410A and $r_2$ 410B cannot be stitched, either because they are not overlapping and/or there are too many sequencing errors, the paired reads are concatenated to form fragment s 405, where reverse complementing $r_2$ 410B converts both read into the same strand (line 3 of Example 2, FIG. 4C). A non-alphabetical character that would not be contained in any kmer is arbitrarily chosen to prevent the generation of non-existent kmers from the data.

At step 260, fragment s undergoes kmer decomposition. Thus, the fragment s is decomposed to overlapping substrings with length k (i.e., kmers), where in one example the kmer length is any one of 5, 6, 7, 8, 9, 10, 11, 12, 13, 14, 15, 16, 17, 18, 19, or 20 nucleotide bases. Therefore, the decomposition of a single fragment s can generate multiple kmers.

Identifying Gene Ranges

At steps 265 and 270, the kmers on the fragment s are mapped to various genes. For each kmer decomposed from fragment s, the kmer is queried against indexing structure K generated at step 230. A kmer to gene mapping table can be constructed that details the position of a kmer on the fragment s, the position of the kmer on fragment s, and the one or more genes that the kmer is found on. As an example, a gene map corresponding to the kmers can be created as follows in Table 1:

TABLE 1

Example kmer to gene mapping table

| $i^{th}$ kmer | kmer Position on Fragment | Position [Beginning, End] on Fragment | Gene |
|---|---|---|---|
| 1 | $p_1$ | $[p_{b1}, p_{e1}]$ | g |
| 2 | $p_2$ | $[p_{b2}, p_{e2}]$ | g, g' |
| . | . | . | . |
| . | . | . | . |
| . | . | . | . |
| N | $p_N$ | $[p_{bN}, p_{eN}]$ | g' |

In various embodiments, each kmer is one base pair shifted from the previous kmer. For example, the $1^{st}$ kmer (e.g., i=1) can correspond to a position p1 of [1, k] where k is the length of the kmer. The $2^{nd}$ kmer (e.g., i=2) can corresponds to a position p2 of [2, k+1] and so on for the $3^{rd}$, $4^{th}$ ... and Nth kmer.

The data in Table 1 is indexed by kmer (e.g., the ith kmer). The data in Table 1 can be similarly expressed using a gene as the index. Then for each gene g so identified, all positions on fragment s that corresponds to a kmer that is found on gene g can be accumulated.

Given all positions on fragment s that include a kmer that is found on a gene g, gene ranges that correspond to positions on fragment s can be constructed. For example, multiple kmers that are overlapping with one another (also referred to as overlapping kmers) on both the fragment s and a gene g can be combined to generate a gene range. Specifically, the gene ranges on gene g that correspond to kmers of fragment s can be represented as a list of ranges $R_g=(R_{g0}, R_{g1}, \ldots, R_{gn-1})$, where the $i^{th}$ range $R_{gi}=[p_{bi}{}^g, p_{ei}{}^g]$ for $0 \leq p_{bi}{}^g < p_{ei}{}^g \leq |s|$. The length of each range $R_{gi}$ can be expressed as $L_i{}^g=(p_{ei}{}^g - p_{bi}{}^g + 1)$. The notation $p_{bi}{}^g$ represents the beginning position of the $i^{th}$ range on fragment s that is correspondingly found on gene g. The notation $p_{ei}{}^g$ represents the end position of the $i^{th}$ range on fragment s that can be found on gene g. The notation |s| denotes the length of strings.

The ranges included in the list of ranges $R_g$ are sorted in an increasing order according to their increasing position on the fragment s.

Referring again to the example shown in Table 1, an example range $R_{g0}$ of gene g can be expressed as $R_{g0}=[p_{b1}, p_{e2}]$ given that gene g has been identified to correspond to both the first and second kmer in fragments. In other words, the range $R_{g0}$ of gene g can be consolidated from overlapping kmers that have each been identified to correspond to the common gene g.

As pointed out earlier, kmers of a given range of fragment s may come from different regions of a sequence of gene g, causing false positive association of the range with gene g. To reduce the false positive rate, a spanning criterion can be imposed (1): any gene that spans a large portion of either $r_1$ or $r_2$ is identified, where each of these genes then can be paired with the remaining genes to be considered further. As an example, the spanning criterion is a threshold length of nucleotide bases (e.g., large portion refers to greater than 50% of a single nucleotide strand) of either $r_1$ or $r_2$ should belong to one of a fusion genes involved in the fusion event.

In various embodiments, an upper bound of spanning criterion is imposed. An upper-bound is imposed because the overlapping regions of g and g' on s could be double counted. This upper-bound serves as a filtering strategy to eliminate unnecessary inference of how the fragment s may be spanned by both genes. Additionally, imposing an upper bound reduces the search space and speeds up subsequent computations. Meanwhile, the gene pairs under consideration are constrained to have known associations to form fusion pairs but do not expect them to have the exact breakpoints as identified in the literature. Once this upper-bound is satisfied, a tighter bound is calculated by deriving the maximum span of fragment s by combining two range lists of g and g'.

Figure 5:
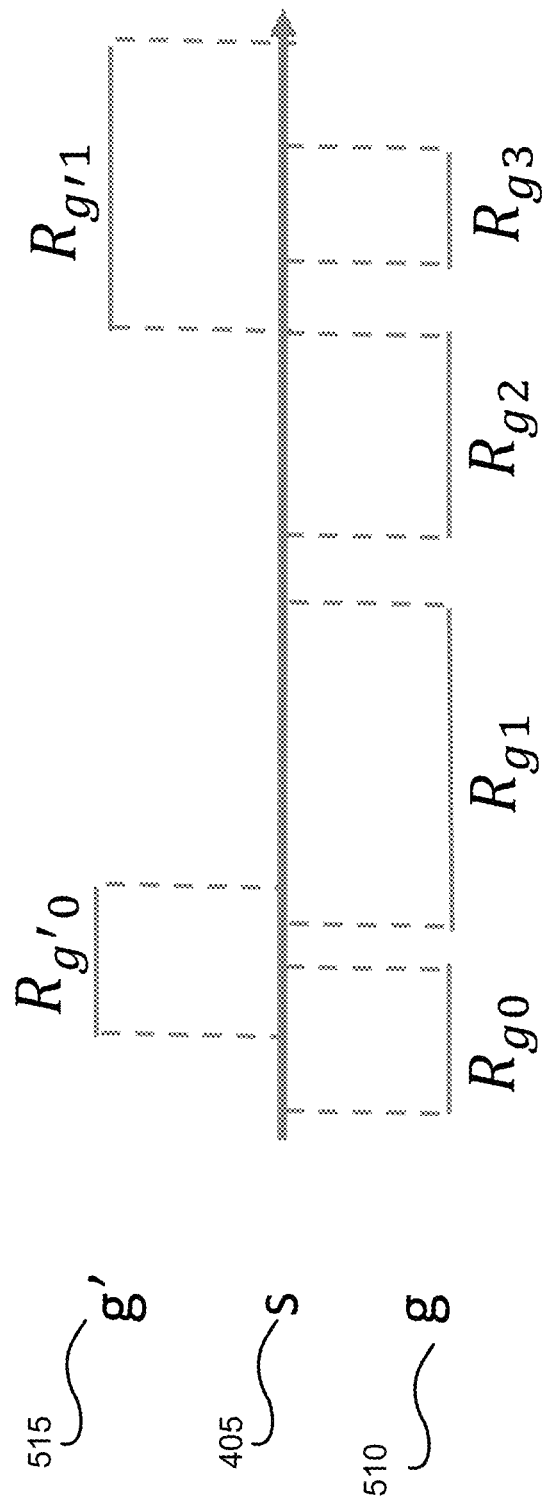
FIG. 5 depicts inferring regions of read fragment s spanned by gene fragments from two genes g and g', in accordance with an embodiment.

For ease of understanding, FIG. 5 depicts an example embodiment of inferring regions of read fragments 405 spanned by gene fragments from two genes g 510 and g' 515. In this particular example, fragments is shown as an arrow and g 510 and g' 515 are two genes inferred to span certain regions of s with each region represented by a short line positioned at the part of s it spans (the range is confined by dotted lines). In various embodiments, further comparisons can be conducted using gene ranges by comparing each gene g and g' with additional genes represented as g", g"', and the like.

As shown in FIG. 5, the fragments 405 is spanned by two ranges on gene g' 515 (e.g., Range $R_{g'0}$ and $R_{g'1}$) and is further spanned by four ranges on gene g 510 (e.g., Ranges $R_{g0}$, $R_{g1}$, $R_{g2}$, and $R_{g3}$).

Determining Maximum Gene Span Using a Support Value

Figure 2:
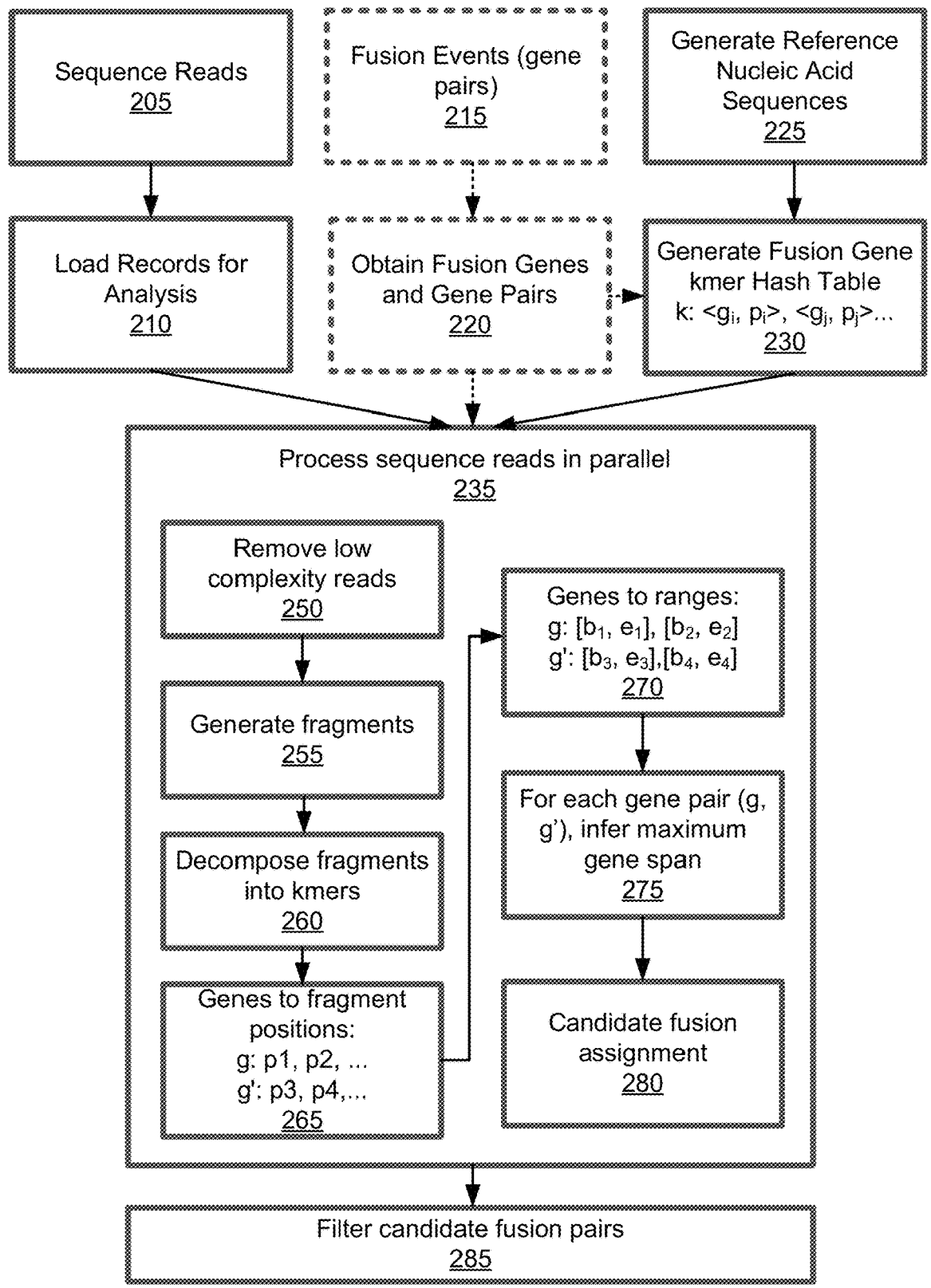
FIG. 2 depicts an overall workflow of identifying fusion pair events, in accordance with an embodiment.

At step 275 shown in FIG. 2, the maximum gene span is inferred for each pair of genes, such as gene pair g and g' shown in FIG. 5. Generally, the maximum gene span for a pair of genes is determined by analyzing the gene ranges on each of the genes in the pair that map to fragment s. The maximum gene span represents the longest spanning gene ranges found on the two genes in the pair (e.g., g and g').

As an example, the gene ranges of gene g and gene g' that have been identified as corresponding to various kmers of fragment s are represented as $R_g=(R_{g0}, R_{g1}, \ldots, R_{gn-1})$ and $R_{g'}=(R_{g'0}, R_{g'1}, \ldots, R_{g'm-1})$, respectively. Gene ranges $R_g$ and $R_{g'}$ are sorted in the increasing order according to their increasing position on the fragment s. The directionality of s is arbitrary as long as it is consistent. Any pair of ranges $R_{gi}=[p_{bi}^g, p_{ei}^g] \in R_g$ and $R_{g'j}=[p_{bj}^{g'}, p_{ej}^{g'}] \in R_{g'}$ defines a possible fusion event.

The maximum gene span is determined based on a support value (e.g., a score) corresponding to each pair of gene ranges, where the two gene ranges in the pair are from differing genes. Generally, the support value determined for a pair of gene ranges is based on the ordering of the gene ranges. For example, given a first gene range from a first gene (e.g., gene g) and the next gene range in the ordering from the second gene (e.g., gene g'), the calculated support value is the sum of the lengths of 1) the first gene range from the first gene, 2) the next gene range in the ordering from the second gene, and 3) all gene ranges on the first gene that are lower ordered in comparison to the first gene range from the first gene. Of note, if the first gene range from the first gene and the next gene range from the gene range overlap, then the overlapping region is eliminated from the support value. Therefore, a support value can be calculated for any two gene ranges, where one of the two gene ranges is from a first gene and the second of two gene ranges is from a second gene.

As a first scenario (referred to hereafter as scenario (1)), the two gene ranges do not overlap with one another on fragments. Therefore, given that $p_{ei}^g < p_{bj}^{g'}$, the support is $\sum_{l=0}^{i} L_l^g + \sum_{l=j}^{m-1} L_l^{g'}$. For example, the support of $R_{g1}$ and $R_{g'1}$ is equal to $L_0^g + L_1^g + L_1^{g'}$ (FIG. 5). Put into words, the support value calculated between the gene range $R_{g1}$ from gene g and $R_{g'1}$, which is the next ordered gene range from gene g', includes the length of gene range $R_{g0}$ (e.g., $L_0^g$) that has a lower (e.g., earlier) order than gene range $R_{g1}$. Additionally, the support value includes the length of $R_{g1}$ (e.g., $L_1^g$) and the length of $R_{g'1}$ (e.g., $L_1^{g'}$).

As a second scenario (referred to hereafter as scenario (2)), the two gene ranges overlap with one another on fragment s. Therefore, given that $p_{ei}^g \geq p_{bi}^{g'}$, the support is $\sum_{l=0}^{i-1} L_l^g + \sum_{l=j+1}^{m-1} L_l^{g'} + (p_{ej}^{g'} - p_{bi}^g + 1)$. For example, the support of $R_{g2}$ and $R_{g'1}$ is equal to $L_0^g + L_1^g + (p_{e1}^{g'} - p_{b2}^g + 1)$ (FIG. 5). Put into words, the support value calculated between $R_{g2}$ and $R_{g'1}$ also includes the lengths of gene ranges $R_{g0}$ and $R_{g1}$ that each are ordered lower (e.g., earlier) than gene range $R_{g2}$. Additionally, given that the gene ranges $R_{g2}$ and $R_{g'1}$ overlap, the support value includes the lengths of gene ranges $R_{g2}$ and $R_{g'1}$ without the overlapping region (e.g., $(p_{e1}^{g'} - p_{b2}^g + 1)$).

Of note, in each of scenario (1) and (2), the lower ordered gene ranges (e.g., $R_{g0}$ in scenario 1, and $R_{g0}$ and $R_{g1}$ in scenario 2) are from a common gene (e.g., gene g). Additionally, although examples (1) and (2) above describe comparisons between a gene range on gene g and a gene range on gene g', a similar comparison to determine a support value can be made between two gene ranges on the same gene.

The maximum span is given by the pair of gene ranges that have the largest support value. Note that either $R_{gi}$ or $R_{g'j}$ is determined to be empty when fragment s is considered to be maximally spanned by either g' or g alone, and the corresponding supports are defined as $\sum_{j=0}^{m-1} L_j^{g'}$ and $\sum_{i=0}^{n-1} L_i^g$, respectively. In various embodiments, gene range comparisons can occur between numerous pairs of genes. For example, if a third gene is represented as g", then gene range comparisons can additionally be conducted between gene ranges in g and g" as well as between gene ranges in g' and g". Therefore, the maximum span can be determined as the gene range comparison between any pair of genes that has the largest support value.

Calculating a maximum span using the support value between a pair of gene ranges provides advantages in processing speed and resource consumption. For example, to calculate all pairwise supports between any two ranges from $R_g$ and $R_{g'}$ would take $\Phi(n*m)$ time which is a function of the n total ranges from $R_g$ and m total ranges from $R_{g'}$. However, based on the following two steps, the time complexity could be reduced to $\Phi(n+m)$: (1) pre-compute prefix and suffix summation of range lengths for $R_g$ and $R_{g'}$ in $\Phi(n)$ and $\Phi(m)$ time, respectively, which can be directly used to calculate support value for each pair, and (2) calculate support only for adjacent pairs in the merged range list of $R_g$ and $R_{g'}$ that are sorted in an increasing order. This can be achieved in $\Phi(n)+\Phi(m)$ time.

Assigning Candidate Fusions

Figure 6:
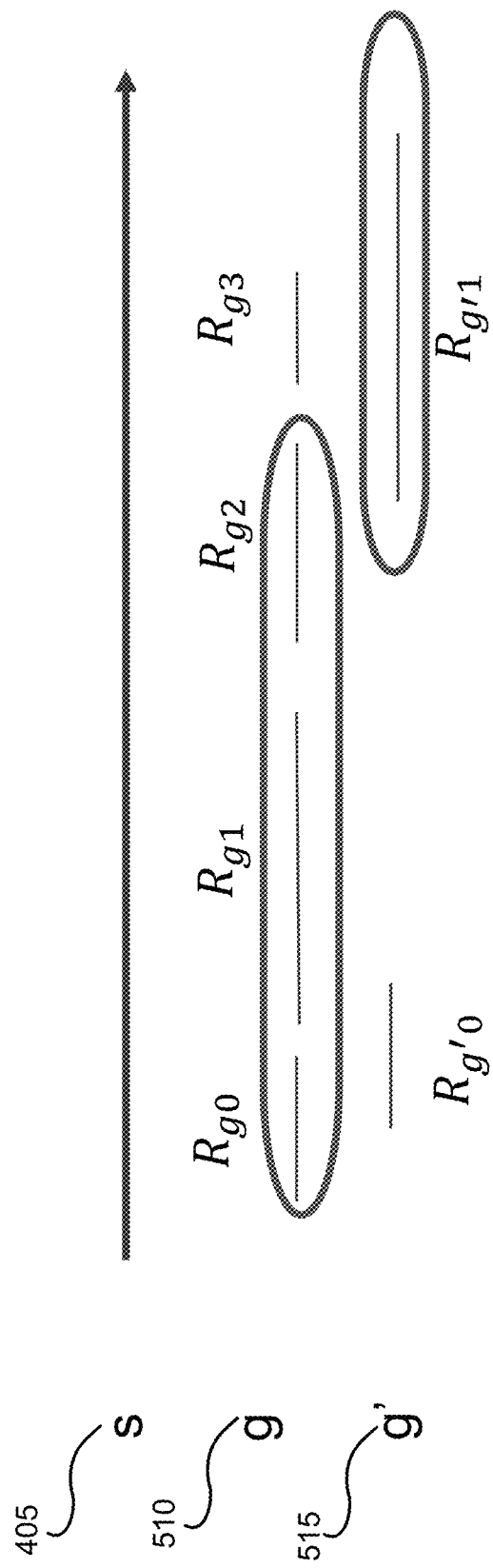
FIG. 6 depicts assigning a candidate fusion event between genes g and g' that correspond to fragment s, in accordance with an embodiment.

At step 280, candidate gene fusions are assigned. For example, the gene pair that yields the maximum gene span inferred for gene pair g and g' can be assigned as a candidate gene fusion. FIG. 6 depicts an example assignment of a candidate gene fusion event between genes g 510 and g' 515 that correspond to fragments 405, in accordance with an embodiment. Here, the maximum gene span may be determined to be the ranges of $R_{g0}$, $R_{g1}$, and $R_{g2}$ from gene g and $R_{g'1}$ from gene g'. Therefore, a candidate gene fusion is assigned between gene pair g 510 and g' 515 given the adjacency of $R_{g2}$ from gene g and $R_{g'1}$ from gene g'.

At step 285, each candidate fusion pair can be further filtered. Filtering includes enforcing one or more additional criteria. One such additional criterion includes that when selecting joint span by two genes, the combined spanning distance (e.g., the length $R_{g0}$, $R_{g1}$, $R_{g2}$, $R_{g'1}$ in the example shown in FIG. 6) needs to be at least a threshold length longer than the span by one of the genes alone. As one example, the threshold length is 25 nucleotide base pairs. As another example, the threshold length is the length of a kmer, as previously described (e.g., length of k nucleotide bases). Another such additional criteria includes that a candidate fusion pair needs to be supported by a minimum number of read pairs such as two.

As another example, filtering criteria can specify a threshold number of genes that a fragment (e.g., fragment s) maps to. For example, if the fragment maps to more than the threshold number of genes, then it may be unlikely that the candidate fusion pair truly reflects a fusion event and the candidate fusion pair can be filtered out.

As yet another example, filtering criteria can specify a threshold overlap between gene ranges of a first gene and a second gene. False positive fusion events can arise from gene ranges of closely related genes. For example, if a range of gene g, which maps to fragment s, shares an overlapping nucleotide sequence that is beyond the threshold overlap with a range of gene g', which also maps to fragment s, then the candidate fusion event identified between gene g and gene g' can be filtered out.

In various embodiments, chimeric reads arising from library preparation artifacts (e.g., PCR template switching, incomplete template extension and mis-hybridization, or other library preparation artifacts) may be identified as candidate fusion events. Therefore, step 285 may employ an exon boundary filter that queries the sequence reads that support a candidate fusion event. The exon boundary filter can be applied in conjunction with either a targeted fusion caller or a de novo fusion caller.

In particular, the exon boundary filter determines whether a breakpoint identified on the sequence read corresponds to an RNA fusion event that likely derived from an in vivo DNA breakpoint and not a library preparation artifact. Generally, if the breakpoint of the sequence read occurs at the boundary between two exon junctions, then the sequence read can be maintained. Conversely, if a breakpoint of the sequence read occurs within the exon bodies, then the sequence read corresponding to the breakpoint is more likely to be an artifact and can be filtered out and removed.

More specifically, the exon boundary filter identifies a threshold number of nucleotide bases adjacent to the breakpoint of the sequence read. In one embodiment, the exon boundary filter may identify a threshold number of nucleotide bases upstream to the breakpoint and further identifies a threshold number of nucleotide bases downstream to the breakpoint. In various embodiments, the threshold number of nucleotides is 2, 3, 4, 5, 6, 7, 8, 9, 10, or more nucleotide bases. Given the identified nucleotide bases within the threshold number of nucleotides of the breakpoint, the identified nucleotide bases are compared to regions in each gene identified by the AF4 caller as involved in the candidate fusion event. In various embodiments, the identified nucleotide bases are compared to exonic regions in each gene. For example, the identified nucleotide bases upstream to the breakpoint can be compared to the 3' ends of all annotated exons for the upstream gene partner, and the identified nucleotide bases downstream to the breakpoint can be compared to 5' ends of all annotated exons for the downstream gene partner. If the comparison yield an alignment in the correct orientation (e.g., the comparison yields a match or the comparison yields a match between at least a threshold number of base pairs), the sequence read is re-annotated to denote the presence of the alignment. In one embodiment, if either the identified nucleotide bases upstream to the breakpoint match the 3' ends of exons for the upstream gene partner or the identified nucleotide bases downstream to the breakpoint match the 5' ends of exons for the downstream gene partner, then the sequence read is re-annotated to denote the alignment. In some embodiments, the sequence read is annotated to denote an alignment if both the identified nucleotide bases upstream to the breakpoint match the 3' ends of exons for the upstream gene partner and the identified nucleotide bases downstream to the breakpoint match the 5' ends of exons for the downstream gene partner. An annotated sequence read that denotes an alignment indicates that the breakpoint in the sequence read that supports the candidate fusion event is more likely to have arisen from an in vivo DNA breakpoint. Sequence reads corresponding to candidate fusion events that are not annotated can be filtered and removed as it is possible that these sequence reads arose from a library preparation artifact.

By applying the exon boundary filter, a candidate fusion event is deemed as a false positive fusion event if less than a threshold number of sequence reads support the candidate fusion event after applying the exon boundary filter. In some embodiments, the threshold number of sequence reads supporting a candidate fusion event is two. In other embodiments, the threshold number of sequence reads support a candidate fusion event is one, three, four, five, or more sequence reads.

Candidate fusion pairs that remain after filtering can be the basis for calling a candidate fusion event.

Pre-Filtering Sequence Reads

Figure 7:
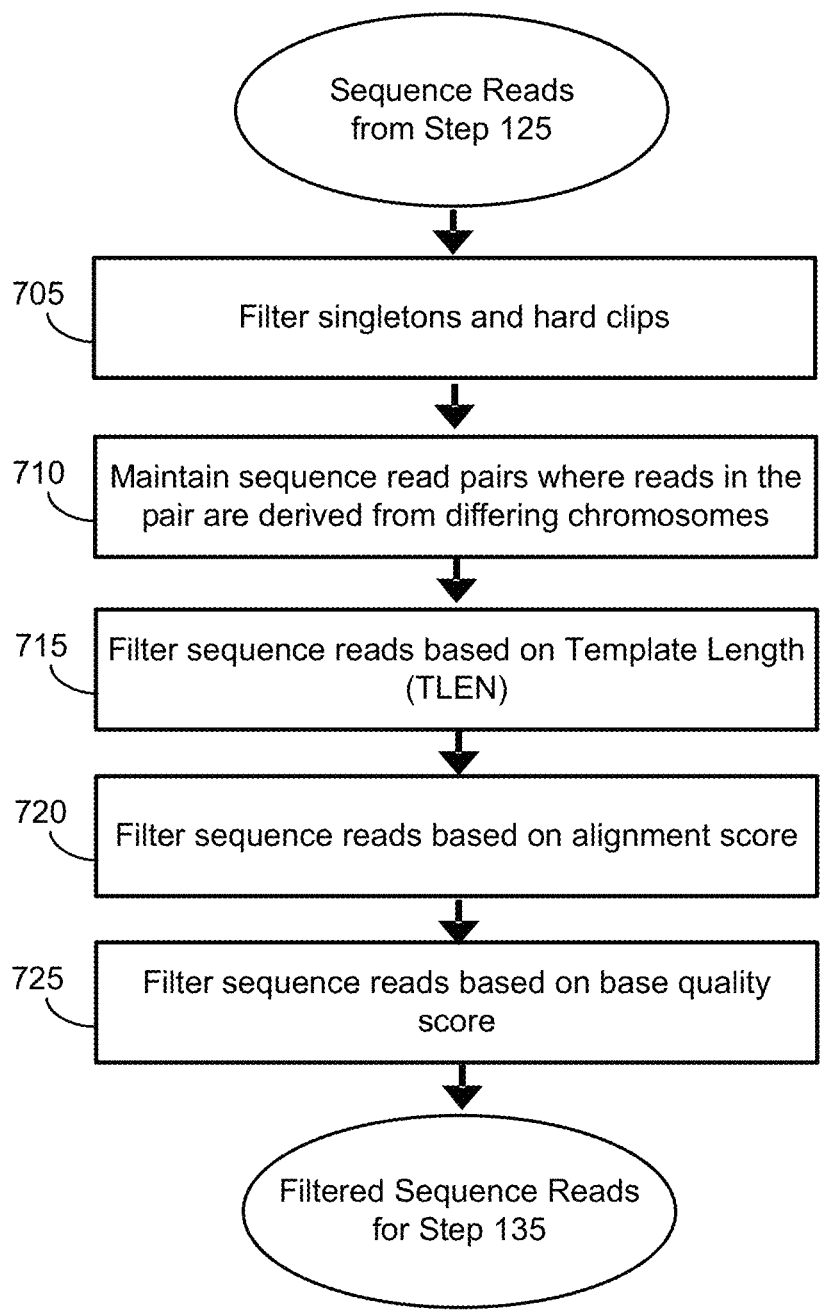
FIG. 7 depicts a pre-filtering process for removing sequence reads, in accordance with an embodiment.

FIG. 7 depicts a pre-filtering process 130 for removing sequence reads that meet one or more criteria, in accordance with an embodiment. Examples of the criteria include, but are not limited to: identifying whether a sequence read is a singleton, identifying whether a sequence read is a hard clip, filtering based on a template length (TLEN) (e.g., a threshold TLEN), filtering based on an alignment score (e.g., a threshold alignment score), or filtering based on a base quality score (e.g., a threshold of a median or mean base quality score). Another criteria includes determining that if a sequence read pair meets the criterion that the reads of the read pair are from differing chromosomes, then the sequence read pair is maintained and not filtered out. Additional examples of criteria include filtering based on a bit flag, a cigar, an edit distance (e.g., a minimum or maximum edit distance), a suboptimal alignment score, or a supplementary alignment measure.

In some embodiments, the pre-filtering process 130 involves removing sequence reads generated at step 125 that meet one or more criteria to identify a subset of filtered sequence reads that can be used at step 135 to call fusion events. In some embodiments, the pre-filtering process 130 additionally or alternatively involves maintaining sequence reads generated at step 125 that meet one or more criteria. In various embodiments, additional or fewer steps than shown in FIG. 7 for filtering sequence reads that meet one or more criteria can be implemented. Additionally, although FIG. 7 depicts a flow process where each of steps 705-725 are shown to be performed in series, in various embodiments, one or more of the different steps 705-725 can be performed in parallel. For example, steps 710, 715, and 720 may be performed in parallel and the resulting, non-filtered sequence reads can then be further analyzed at step 725.

As shown in FIG. 7, at step 705, singletons and hard clips are filtered out. A singleton refers to a single read of a read pair. Without the second read of a read pair, a singleton is not informative for identifying a fusion event and can be readily filtered out. A hard clip refers to a sequence read that has been truncated. Here, a hard-clipped sequence read can lead to the identification of false positive fusion events and therefore, are filtered out.

At step 710, sequence read pairs where the first read and the second read are from differing chromosomes are maintained. In various embodiments, the first read and the second read can be determined to be from differing chromosomes by aligning the first read and the second read to known sequences of chromosomes (e.g., a reference genome). Given that sequence read pairs where the first read and the second read are from differing chromosomes are likely indicative of a fusion event, such sequence read pairs are maintained so that they can be subsequently analyzed. In various embodiments, sequence read pairs that are identified and maintained here at step 710 are further maintained through steps 715, 720, and 725. This ensures that these sequence read pairs are definitively analyzed for a likelihood of a fusion event as opposed to being filtered out.

At step 715, sequence reads are filtered based on the template length (TLEN) for each sequence read. Generally, sequence reads with TLENs greater than a threshold TLEN are maintained whereas sequence reads with TLENs less than the threshold TLEN are filtered and removed. The threshold TLEN can be one of 50, 100, 200, 300, 400, or 500.

At step 720, sequence reads are filtered based on the alignment score for each sequence read. The alignment score for a sequence read captures information about how well a read aligns to a reference genome by capturing information such as matches, mismatches, open gaps (e.g., extends), clipping and improper pairs. As an example, the alignment score (AS) can be expressed as:

$$AS = (1*matches) - (4*mismatches) - (6*opens) - (1*extends) - (5*clipped) - (17*improper\_pair)$$

Therefore, a high alignment score represents a well-aligned sequence read whereas a low alignment score represents a poorly aligned sequence read. Generally, a poorly aligned sequence read is more likely to indicate a presence of a fusion event whereas a well-aligned sequence read is less likely to indicate a presence of a fusion event.

A sequence read is filtered by comparing the alignment score for the sequence read to a threshold alignment score. Generally, sequence reads with alignment scores less than a threshold alignment score are maintained whereas sequence reads with alignment scores greater than the threshold alignment score are filtered and removed. In various embodiments, the threshold alignment score is one of 50, 75, 100, 125, or 140. In particular embodiments, the threshold alignment score is 130.

At step 725, sequence reads are filtered based on the base quality score for each sequence read. Here, the base quality for a sequence read refers to the Phred quality score of nucleotide bases within the sequence read. In one embodiment, the base quality score is represented by a median base quality score, which is calculated as the median of Phred quality scores of nucleotide bases of the sequence read. Generally, sequence reads that each have a median base quality score greater than a threshold median base quality score are maintained whereas sequence reads that each have a median base quality score less than the threshold base quality score are filtered and removed. In various embodiments, the threshold alignment score is one of 10, 25, 35, or 40. In particular embodiments, the threshold alignment score is 30.

Computer Implementation

Figure 8:
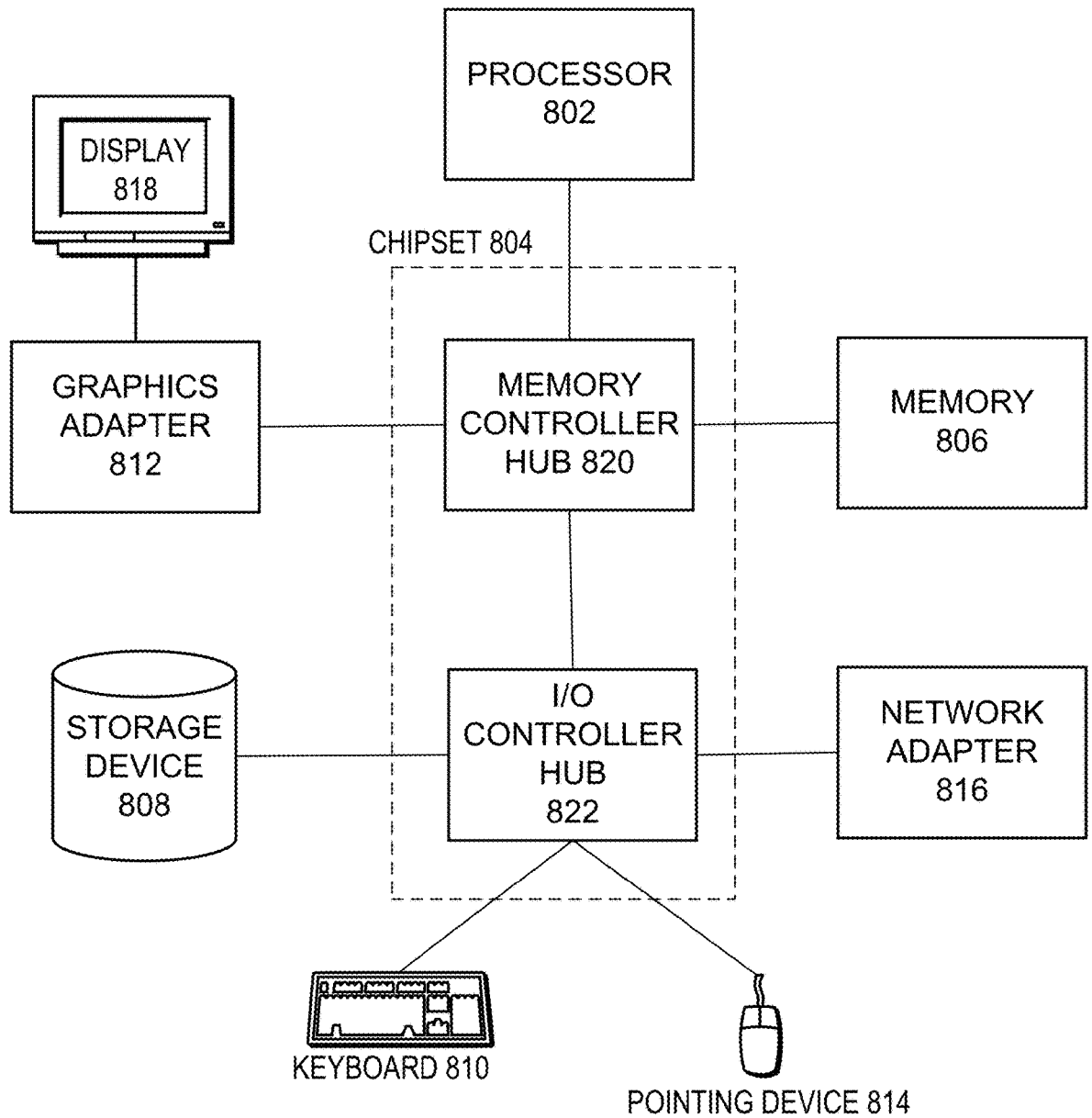
FIG. 8 is a high-level block diagram illustrating physical components of a computer used as part or all of one or more of the entities described herein in one embodiment.

FIG. 8 is a high-level block diagram illustrating physical components of a computer 800 used as part or all of one or more of the entities described herein in one embodiment. Although FIG. 8 depicts a computer 800, the figure is intended as functional description of the various features which may be present in computer systems than as a structural schematic of the implementations described herein. In practice, and as recognized by those of ordinary skill in the art, items shown separately could be combined and some items could be separated.

For example, instances of the illustrated computer 800 may be a computing device that performs steps of the example flow process 100 for processing a test sample. Specifically, the computer 800 can perform step 130 (e.g., pre-filtering sequence reads) and/or step 135 (e.g., calling a fusion event using the sequence reads using the targeted/de novo AF4 caller). Illustrated in FIG. 8 are at least one processor 802 coupled to a chipset 804. Also coupled to the chipset 804 are a memory 806, a storage device 808, a keyboard 810, a graphics adapter 812, a pointing device 814, and a network adapter 816. A display 818 is coupled to the graphics adapter 812. In one embodiment, the functionality of the chipset 804 is provided by a memory controller hub 820 and an I/O hub 822. In another embodiment, the memory 806 is coupled directly to the processor 802 instead of the chipset 804. In some embodiments, the computer 800 includes one or more communication buses for interconnecting these components. The one or more communication buses optionally include circuitry (sometimes called a chipset) that interconnects and controls communications between system components.

The storage device 808 is any non-transitory computer-readable storage medium, such as a hard drive, compact disk read-only memory (CD-ROM), DVD, or a solid-state memory device or other optical storage, magnetic cassettes, magnetic tape, magnetic disk storage or other magnetic storage devices, magnetic disk storage devices, optical disk storage devices, flash memory devices, or other non-volatile solid state storage devices. Such a storage device 808 can also be referred to as persistent memory. The pointing device 814 may be a mouse, track ball, or other type of pointing device, and is used in combination with the keyboard 810 to input data into the computer 800. The graphics adapter 812 displays images and other information on the display 818. The network adapter 816 couples the computer 800 to a local or wide area network. The memory 806 holds instructions and data used by the processor 802. The memory 806 can be non-persistent memory, examples of which include high-speed random access memory, such as DRAM, SRAM, DDR RAM, ROM, EEPROM, flash memory.

As is known in the art, a computer 800 can have different and/or other components than those shown in FIG. 8. In addition, the computer 800 can lack certain illustrated components. In one embodiment, a computer 800 acting as a server may lack a keyboard 810, pointing device 814, graphics adapter 812, and/or display 818. Moreover, the storage device 808 can be local and/or remote from the computer 800 (such as embodied within a storage area network (SAN)).

As is known in the art, the computer 800 is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device 808, loaded into the memory 806, and executed by the processor 802.

Kit Implementation

Also disclosed herein are kits performing the methods described above, including the method of identifying candidate fusion events from a test sample obtained from a subject. Such kits can include reagents for isolating nucleic acids from a test sample. The reagents can further include reagents for sequencing the nucleic acids including buffers and detection agents.

A kit can further include instructions for use of the reagents included in the kit. For example, a kit can include instructions for extracting the nucleic acid from the test sample. Example instructions can be the order in which reagents are to be added, centrifugal speeds to be used to isolate nucleic acids from the test sample, and/or how to operate a computing device, such as computer 800 shown in FIG. 8, for the purposes of performing the steps of the AF4 caller to identify fusion events. In addition to the above components, kits further include instructions of computer software for identifying fusion events.

One form in which these instructions can be present is as printed information on a suitable medium or substrate, e.g., a piece or pieces of paper on which the information is printed, in the packaging of the kit, in a package insert. Yet another means would be a computer readable medium, e.g., diskette, CD, hard-drive, network data storage, on which the instructions have been stored in the form of computer code. Yet another means that can be present is a website address which can be used via the internet to access the information at a removed site.

EXAMPLES

Example 1: Calling Fusions Using the RNA Fusion Caller

The performance of the targeted and de novo RNA fusion caller was compared to the performance of state of the art fusion callers such as ChimerScope and Pizzly. Each of ChimerScope, Pizzly, and the AF4 caller (through either targeted or de novo methods) were employed to detect gene fusions in synthetically generated data that includes two types of fusions: broken exon fusions and intact exon fusions.

Specifically, the synthetically generated data included a total of 70 broken exon fusions and 80 intact exon fusions for a total of 150 detectable fusion events. Additionally, synthetic data were generated with five different coverages (5×, 20×, 50×, 100×, and 200×), each with three different read lengths (50 base pairs, 75 base pairs, and 100 base pairs). Each synthetic dataset with lower coverage (e.g., 5×, 20×, 50×, and 100× coverage) were generated by subsampling the 200× synthetic dataset.

Each of the fusion callers was applied to the different synthetic datasets to identify the 150 fusions. Tables 1-4 depict the performance of each of the fusion callers. Specifically, the performance of each of the fusion callers was evaluated according to measurable parameters including true positive (TP), false negative (FN), false positive (FP), precision, recall, false discovery rate (FDR), and F1 score. Generally, the AF4 caller, specifically both the de novo and the targeted fusion callers described herein, outperformed both the ChimerScope and Pizzly fusion callers.

First, both the targeted and de novo AF4 caller exhibited higher sensitivity in detecting fusion events. Specifically, of the 150 detectable fusions events in the dataset, the de novo AF4 caller detected an average of 147.1 fusion events and the targeted AF4 caller detected an average of 146.5 fusion events. In comparison, the ChimerScope fusion caller detected an average of 132.4 fusion events whereas the Pizzly fusion caller detected an average of 117.2 fusion events.

Second, both the targeted and de novo AF4 caller exhibited higher specificity in comparison to ChimerScope and Pizzly. Specifically, the de novo AF4 caller identified, on average, 2.87 false negatives and 1.33 false positives and the targeted AF4 caller identified, on average, 3.5 false negatives and 0 false positives. In contrast, ChimerScope identified, on average, 17.6 false negatives and 12.67 false positives whereas Pizzly identified, on average, 32.8 false negatives and 12.5 false positives. Finally, both the targeted and de novo AF4 caller achieved a 0.99 F1 score. Here, the F1 score is a measure of the accuracy of the fusion caller and represents a weighted average of the precision and recall (e.g., F1 score=2*(precision*recall)/(precision+recall)). The F1 score achieved by the AF4 caller represents a significant improvement over ChimerScope, which achieved a 0.90 F1 score, and Pizzly, which achieved a 0.84 F1 score.

Of note, the targeted AF4 caller exhibited an average runtime of 14.8 seconds. This is significantly faster than ChimerScope and Pizzly. The de novo AF4 caller exhibited a longer runtime of 14 minutes and 20 seconds, though this is expected given the extensive search performed by the algorithm across the full genome.

Example 2: DNA Fusion Caller

The performance of the targeted DNA fusion caller described above (e.g., the process 135 shown in FIG. 2) was compared to the performance of state of the art DNA fusion callers such as Manta. Specifically, Table 5 details the performance of the targeted AF4 caller and Manta fusion caller for detecting fusion events in DNA samples (e.g., samples 1-14). In particular, the targeted AF4 caller was implemented with pre-filtering (e.g., the pre-filtering process 130 described above in accordance with FIG. 1 and FIG. 7) or without pre-filtering. The performance of each fusion caller was measured according to the number of detected true positives (TP), false positives (FP), and false negatives (FN).

DNA samples were prepared by spiking concentrations of known fusion events. The reference standard used for the study was Horizon Discovery control HD753 (Horizon Discovery Group PLC, Cambridge, United Kingdom)

titrated into a human cell line DNA samples from the Coriell Cell Repository (Coriell Institute, New Jersey, USA) that was characterized by the Genome in a Bottle Consortium (GIAB), GIAB sample NA12878. Horizon control HD753, which includes two known fusion events (RET, chr. 10, CCDC6/RET fusion; and ROS1, chr.4:chr.6, SLC34A2/ROS1 fusion), was titrated into NA12878 at 6 defined concentration levels (0.1%, 0.2%, 0.4%, 0.6%, 0.8%, and 1%).

In general, the targeted AF4 caller, when implemented with either a pre-filter or without a pre-filter, outperformed the Manta fusion caller. First, on average, the targeted AF4 caller, when implemented with either a pre-filter or without a pre-filter, successfully called 1.9 of the 2 expected fusion events whereas the Manta fusion caller successfully called, on average, 1.6 of the 2 expected fusion events. Additionally, the targeted AF4 caller, when implemented without a pre-filter, exhibited an average of 10.8 false positives per sample whereas the targeted AF4 caller, when implemented with a pre-filter, exhibited an average of 4.1 false positives per sample. In contrast, the Manta fusion caller exhibited a large number of false positives (e.g., ~16,380) per sample. Therefore, when benchmarked against the Manta fusion caller, the targeted AF4 caller (with or without prefiltering) is able to deliver improved sensitivity without sacrificing specificity.

The implementation of the targeted AF4 caller with pre-filtering also significantly reduced the runtime of the targeted AF4 caller in comparison to the targeted AF4 caller without prefiltering. Specifically, in comparison to the targeted AF4 caller implemented without prefiltering, the targeted AF4 caller implemented with prefiltering exhibited a nearly 80% reduction in runtime (e.g., 24 hour runtime vs. 5 hour runtime).

Example 3: Exon Boundary Filter Applied for the RNA AF4 Caller

A healthy cfRNA sample was divided into eight separate samples and each separate sample was spiked with differing concentrations of a H2228 cell line, which contains an echinoderm microtubule associated protein like 4 (EML4)—anaplastic lymphoma kinase (ALK) fusion event. Specifically, the eight separate cfRNA samples were spiked at concentrations of 0%, 0.01%, 0.05%, 0.1%, 0.5%, 1%, 10%, and 100% H2228 cell line RNA. The eight separate cfRNA samples were analyzed using the targeted RNA AF4 caller, either with the exon boundary filter or without the exon boundary filter, to identify candidate fusion events present in each of the eight separate cfRNA samples.

The exon boundary filter identifies a breakpoint in sequence reads that support a candidate fusion event and matches the 19 nucleotide bases upstream to the breakpoint and 19 nucleotide bases downstream to the breakpoint to the 3' ends of exons for the upstream gene partner and the 5' ends of exons for the downstream gene partner, respectively. If the comparison yields that neither the 19 upstream nucleotide bases nor the 19 downstream nucleotide bases match the sequences in the upstream and downstream gene partners, respectively, the sequence read is removed as a false positive. Candidate fusion events that are supported by two or greater supporting sequence reads are deemed true positive fusion events.

Figure 9:
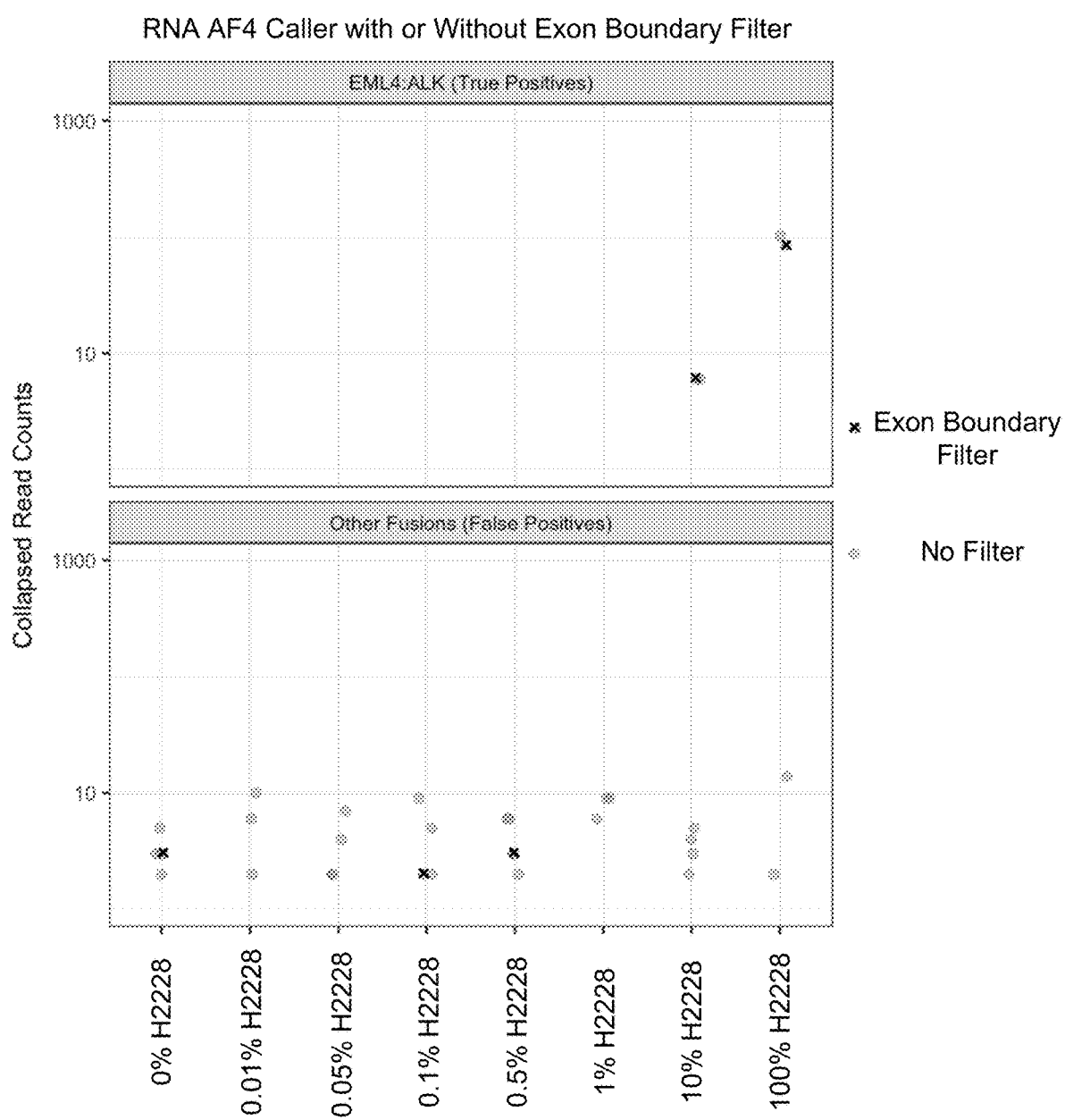
FIG. 9 depicts true and false positive fusion events identified in the eight separate cfRNA samples by the RNA AF4 caller that additionally includes or withholds the exon boundary filter.

FIG. 9 includes two panels that depicts true and false positive fusion events identified in the eight separate cfRNA samples by the RNA AF4 caller that additionally includes or withholds the exon boundary filter. The y-axis of each panel shows the coverage (e.g., read counts) of identified fusion events whereas the x-axis of each panel denotes the % H2228 cell line RNA in each separate cfRNA sample.

The top panel of FIG. 9 depicts the identification of true positive fusion events. Specifically, the EML4:ALK is detected in the 100% H2228 cell line sample and the 10% diluted, 10% H2228 cell line sample with and without implementation of the exon boundary filter. Here, the implementation of the exon boundary filter results in minimal loss in read counts.

The bottom panel of FIG. 9 depicts the identification and filtering of false positive fusion events, categorized as false positives because they are not annotated as being present in the background cfRNA or the spike-in H2228 cell line RNA. Specifically, when the exon boundary filter is not implemented, the AF4 caller identified 27 false positive fusion events across the eight separate samples. The additional implementation of the exon boundary filter reduced the number of identified false positive fusion events to a total of 3 false positive fusion events.

Additional Considerations

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Any of the steps, operations, or processes described herein may be performed or implemented with one or more hardware or software modules of the apparatus, alone or in combination with other devices. In one embodiment, a software module is implemented with a computer program product comprising a computer-readable medium containing computer program code, which can be executed by a computer processor for performing any or all of the steps, operations, or processes described.

It will be understood that various details of the present invention may be changed without departing from the scope of the present invention. Furthermore, the foregoing description is for the purpose of illustration only, and not for the purpose of limitation.

Tables

TABLE 1

Detecting fusions from RNA sequences using de novo Alignment Free Filtering Fusion Fragment (AF4) Caller.

| AF4 De Novo | Runtime | Expected | Detected | TP | FN | FP | Precision | Recall | FDR | F1 score |
|---|---|---|---|---|---|---|---|---|---|---|
| 50bp__5X | 14 m 9 s | 150 | 148 | 147 | 3 | 1 | 0.99 | 0.98 | 0.01 | 0.99 |
| 50bp__20X | 14 m 20 s | | 151 | 149 | 1 | 2 | 0.99 | 0.99 | 0.01 | 0.99 |
| 50bp__50X | 14 m 21 s | | 151 | 149 | 1 | 2 | 0.99 | 0.99 | 0.01 | 0.99 |
| 50bp__100X | 14 m 46 s | | 151 | 149 | 1 | 2 | 0.99 | 0.99 | 0.01 | 0.99 |
| 50bp__200X | 14 m 19 s | | 151 | 149 | 1 | 2 | 0.99 | 0.99 | 0.01 | 0.99 |
| 75bp__5X | 14 m 0 s | | 145 | 144 | 6 | 1 | 0.99 | 0.96 | 0.01 | 0.98 |
| 75bp__20X | 14 m 18 s | | 148 | 147 | 3 | 1 | 0.99 | 0.98 | 0.01 | 0.99 |
| 75bp__50X | 14 m 15 s | | 148 | 147 | 3 | 1 | 0.99 | 0.98 | 0.01 | 0.99 |
| 75bp__100X | 14 m 19 s | | 150 | 148 | 2 | 2 | 0.99 | 0.99 | 0.01 | 0.99 |
| 75bp__200X | 14 m 21 s | | 150 | 148 | 2 | 2 | 0.99 | 0.99 | 0.01 | 0.99 |
| 100bp__5X | 14 m 26 s | | 142 | 142 | 8 | 0 | 1.00 | 0.95 | 0.00 | 0.97 |
| 100bp__20X | 14 m 31 s | | 148 | 147 | 3 | 1 | 0.99 | 0.98 | 0.01 | 0.99 |
| 100bp__50X | 14 m 17 s | | 148 | 147 | 3 | 1 | 0.99 | 0.98 | 0.01 | 0.99 |
| 100bp__100X | 14 m 12 s | | 148 | 147 | 3 | 1 | 0.99 | 0.98 | 0.01 | 0.99 |
| 100bp__200X | 14 m 30 s | | 148 | 147 | 3 | 1 | 0.99 | 0.98 | 0.01 | 0.99 |
| AVG | 14 m 20 s | | 148.5 | 147.1 | 2.87 | 1.33 | 0.99 | 0.98 | 0.01 | 0.99 |

TABLE 2

Detecting fusions from RNA sequences using the targeted Alignment Free Filtering Fusion Fragment (AF4) Caller.

| AF4 Targeted | Runtime | Expected | Detected | TP | FN | FP | Precision | Recall | FDR | F1 score |
|---|---|---|---|---|---|---|---|---|---|---|
| 50bp__5X | 13 s | 150 | 146 | 146 | 4 | 0 | 1.00 | 0.97 | 0.00 | 0.99 |
| 50bp__20X | 14 s | | 147 | 147 | 3 | 0 | 1.00 | 0.98 | 0.00 | 0.99 |
| 50bp__50X | 15 s | | 147 | 147 | 3 | 0 | 1.00 | 0.98 | 0.00 | 0.99 |
| 50bp__100X | 16 s | | 147 | 147 | 3 | 0 | 1.00 | 0.98 | 0.00 | 0.99 |
| 50bp__200X | 18 s | | 147 | 147 | 3 | 0 | 1.00 | 0.98 | 0.00 | 0.99 |
| 75bp__5X | 14 s | | 144 | 144 | 6 | 0 | 1.00 | 0.96 | 0.00 | 0.98 |
| 75bp__20X | 13 s | | 147 | 147 | 3 | 0 | 1.00 | 0.98 | 0.00 | 0.99 |
| 75bp__50X | 14 s | | 147 | 147 | 3 | 0 | 1.00 | 0.98 | 0.00 | 0.99 |
| 75bp__100X | 15 s | | 147 | 147 | 3 | 0 | 1.00 | 0.98 | 0.00 | 0.99 |
| 75bp__200X | 17 s | | 147 | 147 | 3 | 0 | 1.00 | 0.98 | 0.00 | 0.99 |
| 100bp__5X | 13 s | | 144 | 144 | 6 | 0 | 1.00 | 0.96 | 0.00 | 0.98 |
| 100bp__20X | 14 s | | 147 | 147 | 3 | 0 | 1.00 | 0.98 | 0.00 | 0.99 |
| 100bp__50X | 14 s | | 147 | 147 | 3 | 0 | 1.00 | 0.98 | 0.00 | 0.99 |
| 100bp__100X | 15 s | | 147 | 147 | 3 | 0 | 1.00 | 0.98 | 0.00 | 0.99 |
| 100bp__200X | 17 s | | 147 | 147 | 3 | 0 | 1.00 | 0.98 | 0.00 | 0.99 |
| AVG | 14.8 s | | 146.5 | 146.5 | 3.5 | 0 | 1.00 | 0.98 | 0.00 | 0.99 |

TABLE 3

Detecting fusions from RNA sequences using ChimeRScope Fusion Caller

| ChimeRScope | Runtime | Expected | Detected | TP | FN | FP | Precision | Recall | FDR | F1 score |
|---|---|---|---|---|---|---|---|---|---|---|
| 50bp__5X | 10 s | 150 | 135 | 128 | 22 | 7 | 0.95 | 0.85 | 0.05 | 0.90 |
| 50bp__20X | 40 s | | 146 | 134 | 16 | 12 | 0.92 | 0.89 | 0.08 | 0.91 |
| 50bp__50X | 1 m 41 s | | 148 | 134 | 16 | 14 | 0.91 | 0.89 | 0.09 | 0.90 |
| 50bp__100X | 3 m 22 s | | 158 | 133 | 17 | 25 | 0.84 | 0.89 | 0.16 | 0.86 |
| 50bp__200X | 5 m 44 s | | 159 | 133 | 17 | 26 | 0.84 | 0.89 | 0.16 | 0.86 |
| 75bp__5X | 7 s | | 135 | 128 | 22 | 7 | 0.95 | 0.85 | 0.05 | 0.90 |
| 75bp__20X | 27 s | | 141 | 131 | 19 | 10 | 0.93 | 0.87 | 0.07 | 0.90 |
| 75bp__50X | 67 s | | 145 | 134 | 16 | 11 | 0.92 | 0.89 | 0.08 | 0.91 |
| 75bp__100X | 2 m 15 s | | 148 | 135 | 15 | 13 | 0.91 | 0.90 | 0.09 | 0.91 |
| 75bp__200X | 4 m 30 s | | 150 | 135 | 15 | 15 | 0.90 | 0.90 | 0.10 | 0.90 |
| 100bp__5X | 5 s | | 131 | 125 | 25 | 6 | 0.95 | 0.83 | 0.05 | 0.89 |
| 100bp__20X | 20 s | | 141 | 132 | 18 | 9 | 0.94 | 0.88 | 0.06 | 0.91 |
| 100bp__50X | 50 s | | 145 | 134 | 16 | 11 | 0.92 | 0.89 | 0.08 | 0.91 |
| 100bp__100X | 1 m 41 s | | 147 | 135 | 15 | 12 | 0.92 | 0.90 | 0.08 | 0.91 |
| 100bp__200X | 3 m 22 s | | 147 | 135 | 15 | 12 | 0.92 | 0.90 | 0.08 | 0.91 |
| AVG | 1 m 40 s | | 145 | 132.4 | 17.6 | 12.67 | 0.91 | 0.88 | 0.09 | 0.90 |

TABLE 4

Detecting fusions from RNA sequences using Pizzly Fusion Caller.

| Pizzly | Runtime | Expected | Detected | TP | FN | FP | Precision | Recall | FDR | F1 score |
|---|---|---|---|---|---|---|---|---|---|---|
| 50bp_5X | 30 m 7 s | 150 | 131 | 118 | 32 | 13 | 0.90 | 0.79 | 0.10 | 0.84 |
| 50bp_20X | 20 m 14 s | | 141 | 125 | 25 | 16 | 0.89 | 0.83 | 0.11 | 0.86 |
| 50bp_50X | 21 m 31 s | | 141 | 125 | 25 | 16 | 0.89 | 0.83 | 0.11 | 0.86 |
| 50bp_100X | 22 m 57 s | | 143 | 126 | 24 | 17 | 0.88 | 0.84 | 0.12 | 0.86 |
| 50bp_200X | 23 m 50 s | | 144 | 127 | 23 | 17 | 0.88 | 0.85 | 0.12 | 0.86 |
| 75bp_5X | 22 m 7 s | | 111 | 102 | 48 | 9 | 0.92 | 0.68 | 0.08 | 0.78 |
| 75bp_20X | 21 m 13 s | | 132 | 119 | 31 | 13 | 0.90 | 0.79 | 0.10 | 0.84 |
| 75bp_50X | 21 m 27 s | | 137 | 124 | 26 | 13 | 0.91 | 0.83 | 0.09 | 0.86 |
| 75bp_100X | 21 m 52 s | | 137 | 124 | 26 | 13 | 0.91 | 0.83 | 0.09 | 0.86 |
| 75bp_200X | 24 m 38 s | | 138 | 125 | 25 | 13 | 0.91 | 0.83 | 0.09 | 0.87 |
| 100bp_5X | 20 m 6 s | | 94 | 90 | 60 | 4 | 0.96 | 0.60 | 0.04 | 0.74 |
| 100bp_20X | 20 m 12 s | | 120 | 109 | 41 | 11 | 0.91 | 0.73 | 0.09 | 0.81 |
| 100bp_50X | 21 m 24 s | | 125 | 114 | 36 | 11 | 0.91 | 0.76 | 0.09 | 0.83 |
| 100bp_100X | 21 m 44 s | | 125 | 114 | 36 | 11 | 0.91 | 0.76 | 0.09 | 0.83 |
| 100bp_200X | 23 m 25 s | | 127 | 116 | 34 | 11 | 0.91 | 0.77 | 0.09 | 0.84 |
| AVG | 22 m 30 s | | 129.7 | 117.2 | 32.8 | 12.5 | 0.91 | 0.78 | 0.09 | 0.84 |

TABLE 5

Detecting fusions from DNA sequences using the Targeted Alignment Free Filtering Fusion Fragment (AF4) Caller.

| | Spike | | AF4 without prefilter | | | AF4 with prefilter | | | Manta | |
|---|---|---|---|---|---|---|---|---|---|---|
| Sample | Concentration | Expected | TP | FP | FN | TP | FP | FN | TP | FP |
| 1 | 0.001 | 2 | 1 | 11 | 1 | 1 | 5 | 1 | 1 | 21839 |
| 2 | 0.002 | | 1 | 12 | 1 | 1 | 2 | 1 | 0 | 19301 |
| 3 | 0.002 | | 2 | 8 | 0 | 2 | 2 | 0 | 1 | 9705 |
| 4 | 0.004 | | 2 | 11 | 0 | 2 | 5 | 0 | 2 | 28890 |
| 5 | 0.004 | | 2 | 15 | 0 | 2 | 7 | 0 | 2 | 20797 |
| 6 | 0.004 | | 2 | 13 | 0 | 2 | 4 | 0 | 2 | 15931 |
| 7 | 0.006 | | 2 | 10 | 0 | 2 | 3 | 0 | 1 | 8503 |
| 8 | 0.006 | | 2 | 14 | 0 | 2 | 7 | 0 | 2 | 16525 |
| 9 | 0.006 | | 2 | 10 | 0 | 2 | 7 | 0 | 2 | 14188 |
| 10 | 0.008 | | 2 | 9 | 0 | 2 | 2 | 0 | 2 | 16435 |
| 11 | 0.008 | | 2 | 10 | 0 | 2 | 6 | 0 | 2 | 8280 |
| 12 | 0.008 | | 2 | 11 | 0 | 2 | 2 | 0 | 2 | 18632 |
| 13 | 0.010 | | 2 | 10 | 0 | 2 | 4 | 0 | 2 | 19660 |
| 14 | 0.010 | | 2 | 7 | 0 | 2 | 2 | 0 | 2 | 10636 |
| | Average | | 1.9 | 10.8 | 0.1 | 1.9 | 4.1 | 0.1 | 1.6 | 16380 |

What is claimed is:

1. A computer-implemented method for reducing consumption of computer resources in the identification of a candidate gene fusion event from a test sample, the method comprising:

receiving a data set in a computer comprising a processor and a computer-readable medium, wherein the data set comprises a plurality of sequence read pairs obtained by sequencing a test sample comprising millions of individual nucleic acid molecules;

loading an index structure into a memory of the computer, the index structure comprising a hash table comprising hash values generated based on kmers decomposed from fusion-related sequences;

clustering the plurality of sequence read pairs into batches, each batch comprising sequence read pairs of the plurality;

streaming one or more batches into the memory of the computer, the one or more batches comprising sequence read pairs of the plurality and selected based on a number of sequence read pairs that can be computed by the processor in parallel;

executing instructions stored on a computer-readable medium that, when executed by the computer, cause the computer to process each sequence read pair loaded into the memory in parallel, the instructions causing the computer to:

generate a plurality of kmers from the sequence read pairs loaded into the memory, each kmer having a length of k nucleic acids;

query the index structure loaded into the memory with each kmer within the plurality of kmers to determine whether the kmer matches a gene segment of one or more genes;

generate a plurality of gene ranges, each gene range comprising one or more kmers that map to a gene segment from a gene and map to a kmer in the index structure;

determine a maximum gene span between a first gene and a second gene based on the plurality of gene ranges; and assign a candidate gene fusion event to the first gene and the second gene.

2. The method of claim 1, wherein the instructions to generate the plurality of kmers from the plurality of sequence read pairs further comprise instructions that, when executed by the processor, cause the computer to:

process one or more of the plurality of sequence read pairs to generate a plurality of fragments; and for each fragment of the plurality of fragments, decompose the fragment into the plurality of kmers.

3. The method of claim 2, wherein the instructions to process one or more of the plurality of sequence read pairs to generate a plurality of fragments further comprise instructions that, when executed by the processor, cause the computer to:

decompose a sequence read pair comprising a first sequence read and a second sequence read into a plurality of kmers;

identify a common kmer from the plurality of kmers that occurs in the first sequence read and second sequence read; and concatenate a prefix of the first sequence read, the common kmer, and a suffix of the second sequence read.

4. The method of claim 2, wherein the instructions to process one or more of the plurality of sequence read pairs further comprise instructions that, when executed by the processor, cause the computer to:

identify an overlapping region between a first sequence read of a sequence read pair and a second sequence read of the sequence read pair; and trim an overhang of the first sequence read that is beyond the second sequence read.

5. The method of claim 2, wherein the instructions to process one or more of the plurality of sequence read pairs further comprise instructions that, when executed by the processor, cause the computer to concatenate a first sequence read of a sequence read pair with a reverse of a second sequence read of the sequence read pair.

6. The method of claim 1, wherein the instructions to determine the maximum gene span further comprise instructions that, when executed by the processor, cause the computer to:

for one or more pairs of gene ranges of the plurality of gene ranges, determine a score for each pair of gene ranges, wherein each of the one or more pairs of gene ranges are derived from two different genes; and determine a maximally scored pair of gene ranges, the maximally scored pair of gene ranges derived from the first gene and the second gene.

7. The method of claim 6, wherein the instructions to determine the maximum gene span further comprise instructions that, when executed by the processor, cause the computer to order the plurality of gene ranges based on a position of each gene range.

8. The method of claim 6, wherein the score determined for each pair of gene ranges comprises a summation of a length of a first gene range of the pair of gene ranges, a length of a second gene range of the pair of gene ranges, and one or more lengths of gene ranges that have a lower order in comparison to the first gene range.

9. The method of claim 8, wherein each of the first gene range and gene ranges corresponding to the one or more lengths of gene ranges are derived from a common gene.

10. The method of claim 8, wherein the first gene range corresponds to a first gene and the second gene range is a next ordered gene range relative to the first gene range.

11. The method of claim 10, wherein the second gene range is the next ordered gene range corresponding to the second gene.

12. The method of claim 1, wherein the instructions to determine the maximum gene span further comprise instructions that, when executed by the processor, cause the computer to:

compare a length of the determined maximum gene span to a threshold length; and identify the first gene and the second gene as corresponding to the candidate gene fusion event based on the comparison.

13. The method of claim 1, wherein each kmer corresponding to a hash value stored in the hash table of the index structure is indexed by a fusion-related sequence.

14. The method of claim 13, wherein each kmer corresponding to a hash value stored in the hash table of the index structure is indexed by a start position in the sequence that the kmer is located.

15. The method of claim 13, wherein each kmer corresponding to a hash value stored in the hash table of the index structure is generated by:

extracting a plurality of sequence read pairs from previously identified fusion gene pairs; and decomposing the plurality of extracted sequence read pairs into the kmers corresponding to hash values stored in the hash table of the index structure.

16. The method of claim 1, wherein the computer-readable medium further comprises instructions that, when executed by the processor, cause the computer to:

remove one or more of the plurality of sequence read pairs that are of low complexity, wherein a low complexity sequence read pair includes one or two nucleotides that occur over a threshold percentage of all nucleotides in the sequence read pair.

17. The method of claim 1, wherein the computer-readable medium further comprises instructions that, when executed by the processor, cause the computer to:

remove one or more of the plurality of sequence read pairs that are of low complexity, wherein a low complexity sequence read pair is less than a threshold read length.

18. The method of claim 1, wherein the test sample comprises cell-free RNA nucleic acid fragments, and wherein the plurality of sequence read pairs comprises RNA sequencing reads.

19. The method of claim 1, wherein the test sample comprises cell-free DNA nucleic acid fragments, and wherein the plurality of sequence read pairs comprises DNA sequencing reads.

20. The method of claim 1, wherein each kmer corresponding to a hash value stored in the hash table of the index structure are generated by:

generating a reference nucleic acid sequence by concatenating an exon region with an adjacent intron region; and decomposing the reference nucleic acid sequence comprising at least the concatenated exon and intron regions into kmers.

21. The method of claim 20, wherein generating the reference nucleic acid sequence further comprises concatenating at least one exon sequence with a padding region.

22. The method of claim 21, wherein the padding region comprises between 50-150 base pairs.

23. The method of claim 1, wherein the computer-readable medium further comprises instructions that, when executed by the processor, cause the computer to:

prior to generating the plurality of kmers from the plurality of sequence read pairs, pre-filter the plurality of sequence read pairs to remove sequence read pairs that meet one or more criteria.

24. The method of claim 23, wherein the criteria comprise whether a sequence read is a singleton, whether a sequence read is a hard clip, a threshold template length, a threshold alignment score, a threshold base quality score, a bit flag, a cigar, an edit distance, a suboptimal alignment score, or a supplementary alignment measure.

25. The method of claim 1, wherein the computer-readable medium further comprises instructions that, when executed by the processor, cause the computer to:
   subsequent to assigning the candidate gene fusion event to the first gene and the second gene, apply an exon boundary filter to determine whether the candidate gene fusion event is a false positive fusion gene event.

26. The method of claim 25, wherein the instructions that cause the computer to apply the exon boundary filter further comprise instructions that, when executed by the processor, cause the computer to:
   for each of one or more sequence read pairs of the plurality of sequence read pairs that support the candidate gene fusion event,
      identify a breakpoint of the sequence read pair corresponding to the candidate gene fusion event;
      identify nucleotide bases within a threshold number of nucleotide bases; and
      compare the identified nucleotide bases to regions in the first gene and the second gene.

27. The method of claim 1, wherein the instructions executed by the computer cause the computer to process at least 4,000 sequence reads using less than 15 gigabytes of computer resources per million read pairs.

* * * * *

UNITED STATES PATENT AND TRADEMARK OFFICE
CERTIFICATE OF CORRECTION

| | |
|---|---|
| PATENT NO. | : 11,473,137 B2 |
| APPLICATION NO. | : 16/006704 |
| DATED | : October 18, 2022 |
| INVENTOR(S) | : Yang et al. |

It is certified that error appears in the above-identified patent and that said Letters Patent is hereby corrected as shown below:

On the Title Page

Item (56), in Column 2, under "Other Publications", Line 19, delete "ChineRScope:" and insert --ChimeRScope:--, therefor.

Signed and Sealed this
Twenty-fourth Day of January, 2023

Katherine Kelly Vidal
*Director of the United States Patent and Trademark Office*